US009951111B2

(12) United States Patent
Johnson et al.

(10) Patent No.: US 9,951,111 B2

(45) Date of Patent: Apr. 24, 2018

(54) TYPE I INTERFERON MIMETICS AS THERAPEUTICS FOR CANCER, VIRAL INFECTIONS, AND MULTIPLE SCLEROSIS

(71) Applicant: UNIVERSITY OF FLORIDA RESEARCH FOUNDATION, INC., Gainesville, FL (US)

(72) Inventors: Howard M. Johnson, Gainesville, FL (US); Chulbul M. Ahmed, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

(21) Appl. No.: 14/103,564

(22) Filed: Dec. 11, 2013

(65) Prior Publication Data

US 2014/0134237 A1 May 15, 2014

Related U.S. Application Data

(63) Continuation-in-part of application No. PCT/US2012/043565, filed on Jun. 21, 2012.

(60) Provisional application No. 61/499,495, filed on Jun. 21, 2011.

(51) Int. Cl.

| | |
|---|---|
| ***A61K 39/00*** | (2006.01) |
| ***A61K 38/21*** | (2006.01) |
| ***C07H 21/04*** | (2006.01) |
| ***A61K 9/127*** | (2006.01) |
| ***C07K 14/47*** | (2006.01) |
| ***A61K 38/16*** | (2006.01) |
| ***A61K 38/17*** | (2006.01) |
| ***A61K 31/7088*** | (2006.01) |
| ***A61K 45/06*** | (2006.01) |
| ***C07K 16/28*** | (2006.01) |
| ***C12N 15/113*** | (2010.01) |

(52) U.S. Cl.

CPC .......... *C07K 14/47* (2013.01); *A61K 31/7088* (2013.01); *A61K 38/16* (2013.01); *A61K 38/17* (2013.01); *A61K 38/1709* (2013.01); *A61K 38/21* (2013.01); *A61K 38/212* (2013.01); *A61K 38/215* (2013.01); *A61K 38/217* (2013.01); *A61K 45/06* (2013.01); *C07K 16/2866* (2013.01); *C12N 15/1136* (2013.01)

(58) Field of Classification Search

None

See application file for complete search history.

(56) References Cited

U.S. PATENT DOCUMENTS

| | | | | |
|---|---|---|---|---|
| 5,770,191 | A * | 6/1998 | Johnson ................. | C07K 14/57 424/450 |
| 6,120,762 | A | 9/2000 | Johnson et al. | |
| 6,204,022 | B1 * | 3/2001 | Johnson ................. | C07K 14/56 424/85.4 |
| 7,060,673 | B2 * | 6/2006 | Song ........................ | A61K 8/64 435/69.1 |
| 7,695,710 | B2 | 4/2010 | Villarete et al. | |
| 2006/0165654 | A1 | 7/2006 | Zavyalov et al. | |
| 2012/0316322 | A1 | 12/2012 | Wei | |

FOREIGN PATENT DOCUMENTS

| | | |
|---|---|---|
| KR | 10-2006-0015701 | 2/2006 |
| WO | WO 99/20653 | 4/1999 |
| WO | WO 2010151495 A2 * | 12/2010 |
| WO | WO-2012/177892 | 12/2012 |

OTHER PUBLICATIONS

Kolchanov, 1988, Journal of Molecular Evolution, vol. 27, pp. 154-162.*
Pasquo, 2012, PLoS ONE, vol. 7, Issue 2, e32555.*
Bork, 2000, Genome Research 10:398-400.*
Bork et al., 1996, Trends in Genetics 12:425-427.*
Danilkovich et al. (1991), Immunology Letters, vol. 31, pp. 15-20.*
Ahmed CMI et al., "Selective Expression of Nonsecreted Interferon by an Adenoviral Vector Confers Antiproliferative and Antiviral Properties and Causes Reduction of Tumor Growth in Nude Mice" *Journal of Interferon and Cytokine Research*, 2001, 21:399-408.
Ahmed CM and Johnson HM, "IFN-γ and its receptor subunit IFNGRI are recruited to the IFN-γ-activated sequence element at the promoter site of IFN-γ-activated genes: evidence of transactivational activity in IFNGRI" *The Journal of Immunology*, 2006, 177(1):315-21.

(Continued)

*Primary Examiner* — Vanessa L. Ford
*Assistant Examiner* — Jegatheesan Seharaseyon
(74) *Attorney, Agent, or Firm* — Saliwanchik Lloyd & Eisenschenk

(57) ABSTRACT

The subject invention pertains to agonist peptides of type I interferons and methods of using the peptides. These peptides are based on the amino acid sequence of the C-terminus region of the type I IFN molecules and are capable of binding to the cytoplasmic domain of type I IFN receptors. Surprisingly, these peptides were found to possess the same or similar biological activity as that associated with the full-length, mature type I IFN proteins, even though these peptides do not bind to the extracellular domain of the type I IFN receptors. In one embodiment, the peptide is a peptide of IFNα. In another embodiment, the peptide is a peptide of IFNβ. Exemplified peptides of the invention include those having SEQ ID NO:1, SEQ ID NO:2, SEQ ID NO:3, SEQ ID NO:4, SEQ ID NO:5, SEQ ID NO:6, SEQ ID NO:38, SEQ ID NO:39, and SEQ ID NO:40. The subject peptides have been shown to effect increased resistance to viral infection. Peptides of the invention can be used to treat or prevent viral infections, to treat oncological disorders, and to treat autoimmune disorders, such as multiple sclerosis.

20 Claims, 8 Drawing Sheets

(56) References Cited

OTHER PUBLICATIONS

Ahmed CM et al., "The role of IFNγ nuclear localization sequence in intracellular function" *Journal of Cell Science*, 2003, 116:3089-3098.
Ahmed CM et al., "IFN Mimetic as a Therapeutic for Lethal Vaccinia Virus Infection: Possible Effects on Innate and Adaptive Immune Responses" *The Journal of Immunology*, 2007, 178:4576-4583.
Ahmed CM et al., "Peptide Mimetics of Gamma Interferon Possess Antiviral Properties against Vaccinia Virus and Other Viruses in the Presence of Poxvirus B8R Protein" *Journal of Virology*, 2005, 79(9):5632-5639.
Ahmed CM et al., "I IFN receptor controls activated TYK2 in the nucleus: Implications for EAE therapy" *Journal of Neuroimmunology*, 2013, 254(1-2):101-109.
Arduino PG and Porter SR, "Herpes Simplex Virus Type 1 infection: overview on relevant clinico-pathological features" *Journal of Oral Pathology & Medicine*, 2008, 37(2):107-121.
Begitt A et al., "Nucleocytoplasmic translocation of Stat1 is regulated by a leucine-rich export signal in the coiled-coil domain." *Proceedings of the National Academy of Sciences of the United States of America* (*PNAS*), 2000, 97(19):10418-10423.
Burgos JS et al., "ICP47 mediates viral neuroinvasiveness by induction of TAP protein following intravenous inoculation of herpes simplex virus type 1 in mice" *Journal of NeuroVirology*, 2006, 12:420-427.
Chee AV and Roizman B, "Herpes simplex virus 1 gene products occlude the interferon signaling pathway at multiple sites" *Journal of Virology*. 2004, 78(8):4185-96.
Chen H-M et al., "Critical role for constitutive type 1 interferon signaling in the prevention of cellular transformation" *Cancer Science*, 2009, 100:449-456.
Croker BA et al., "SOCS regulation of the JAK/STAT signalling pathway" *Seminars in Cell & Developmental Biology*, 2008, 19(4):414-22, Epub Jul. 30, 2008.
Cunningham AL et al., "The Cycle of Human Herpes Simplex Virus Infection: Virus Transport and Immune Control" *The Journal of Infectious Diseases*, 2006, 194(1);S11-S18.
Dawson MA et al., "JAK2 phosphorylates histone H3Y41 and excludes HP1α from chromatin" *Nature*, 2009, 461:819-822.
Decman V et al., "Gamma interferon can block herpes simplex virus type 1 reactivation from latency, even in the presence of late gene expression" *Journal of Virology*, 2005, 79(16):10339-10347.
Diefenback RJ et al., "Transport and egress of herpes simplex virus in neurons" *Reviews in Medical Virology*, 2008, 18:35-51.
Dorsky DI and Crumpacker CS, "Drugs five years later: acyclovir" *Annals of Internal Medicine* 1987, 107:859-874.
Duvallet EL et al., "Interleukin-23: A key cytokine in inflammatory diseases" *Annals of Medicine*, 2011, 43:503-511.
Eidson KM et al., "Expression of Herpes Simplex Virus ICP0 Inhibits the Induction of Interferon-Stimulated genes by Viral Infection" *Journal of Virology*, 2002, 76(5):2180-2191.
Frey KG et al., "HSV-1-Induced SOCS-1 Expression in Keratinocytes: Use of a SOCS-1 Antagonist to Block a Novel Mechanism of Viral Immune Evasion" *The Journal of Immunology*, 2009, 183:1253-1262.
Fulcher AJ et al., "Interferon γ is recognised by importin α/β: Enhanced nuclear localising and transactivation activities of an interferon gamma mimetic" *FEBS Letters*, 2008, 582(11):1569-1574.
Goldsmith K et al., "Infected Cell Protein (ICP)47 Enhances Herpes Simplex Virus Neurovirulence by Blocking the CD8$^+$ T Cell Response" *The Journal of Experimental Medicine*, 1998, 187(3):341-348.
Gough DJ et al., "IFNγ signaling—Does it mean JAK-STAT?" *Cytokine & Growth Factor Reviews*, 2008, 19:383-394.
Halford WP et al., "ICP0 antagonizes Stat 1-dependent repression of herpes simplex virus: Implications for the regulation of viral latency" *Virology Journal*, 2006, 3:44-49.
Jager LD et al., "The kinase inhibitory region of SOCS-1 is sufficient to inhibit T-helper 17 and other immune functions in experimental allergic encephalomyelitis" *J. Neuroimmunology*, 2011, 232:108-118.
Johnson HM and Ahmed CM, "Gamma Interferon Signaling: Insights to Development of Interferon Mimetics" *Cellular and Molecular Biology*, 2006, 52:71-76.
Johnson HM et al., "Steroid-like signaling by interferons: making sense of specific gene activation by cytokines" *Biochemical Journal*, 2012, 443(2):329-338.
Johnson HM et al., "Trafficking and signaling pathways of nuclear localizing protein ligands and their receptors" *BioEssays*, 2004, 26(9):993-1004.
Jones LL and Vignali DAA, "Molecular interactions within IL-6/IL-12 cytokine/receptor superfamily" *Immunologic Research*, 2011, 51(1):5-14.
Knickelbein JE et al., "Noncytotoxic Lytic Granule-Mediated CD8$^+$ T Cell Inhibition of HSV-1 Reactivation from Neuronal Latency" *Science*, 2008, 322(5899):268-271.
Kobayashi T et al., "Mal-function of TLRs by SOCS" *Nature Immunology*, 2006, 7:123-124.
Koelle DM and Corey L, "Herpes Simplex: Insights on Pathogenesis and Possible Vaccines" *Annual Review of Medicine*, 2008, 59:381-395.
Kushnaryov VM et al., "Internalization and Transport of Mouse Beta-Interferon into the Cell Nucleus" *J. Interferon Res*., 1986, 6:241-245.
Levy DE and Darnell JE Jr, "STATS: Transcriptional Control and Biological Impact" *Nature Reviews*, 2002, 3:651-662.
Lindgren M et al., "Cell-penetrating peptides" *Trends Pharmacological Sciences*, 2000, 21(3):99-103.
Lobie PE et al., "Constitutive nuclear localization of Janus kinases 1 and 2" *Endocrinology*, 1996, 137(9):4037-4045, abstract only.
Lu X et al., "Dimerization by a Cytokine Receptor is Necessary for Constitutive Activation of JAK2V617F" *J. Biol. Chem*., 2008, 283:5258-5266.
Mansell A et al., "Suppressor of cytokine signaling 1 negatively regulates Toll-like receptor signaling by mediating Mal degradation" *Nature Immunology*, 2006, 7(2):148-155.
McBride KM et al., "Nuclear export signal located within the DNA-binding domain of the STAT1 transcription factor" *The European Molecular Biology Organization Journal*, 2000, 19(22):6196-6206.
Melen K et al., "Arginine/Lysine-rich Structural Element is Involved in Interferon-induced Nuclear Import of STATs" *The Journal of Biological Chemistry*, 2001, 276(19):16447-16455.
Mikloska Z et al., "In Vivo Production of Cytokines and β (C-C) Chemokines in Human Recurrent Herpes Simplex Lesions—Do Herpes Simplex Virus-Infected Keratinocytes Contribute to Their Production?" *The Journal of Infectious Diseases*, 1998, 177(4):827-838.
Moss B and Shisler JL, "Immunology 101 at poxvirus U: Immune evasion genes" *Seminars in Immunology*, 2001, 13(1):59-66.
Mossman K, "Analysis of anti-interferon properties of the herpes simplex virus type 1 ICP0 protein" from Methods in Molecular Medicine, vol. 116: Interferon Methods and Protocols, DJ Carr, ed., Humana Press, Totowa, NJ, 2005, pp. 195-205.
Mujtaba MG et al., "The Gamma Interferon (IFN-γ) Mimetic Peptide IFN-γ (95-133) Prevents Encephalomyocarditis Virus Infection both in Tissue Culture and in Mice" *Clinical and Vaccine Immunology*, 2006, 13(8):944-952.
Nilsson J et al., "Nuclear Jak2 and Transcription Factor NF1-C2: a Novel Mechanism of Prolactin Signaling in Mammary Epithelial Cells" *Mol. Cell. Biol*., 2006, 26:5663-5674.
Noon-Song EN et al., "Controlling nuclear JAKs and STATs for specific gene activation by IFNγ" *Biochemical and Biophysical Research Communications*, 2011, 410(3):648-653.
Patel AR et al., "Treatment of herpes simplex virus infection: rationale for occlusion" *Advanced Skin Wound Care*, 2007, 20:408-412.
Pothlichet JM et al., "Cutting Edge: Innate Immune Response Triggered by Influenza A Virus is Negatively Regulated by SOCS1

(56) References Cited

OTHER PUBLICATIONS and SOCS3 through a RIG-1/IFNAR1-Dependent Pathway" *The Journal of Immunology*, 2008, 180:2034-2038.
Ragimbeau J et al., "The Receptor Interaction Region of Tyk2 Contains a Motif Required for Its Nuclear Localization" *J. Biol. Chem.*, 2001, 276:30812-30818.
Sheridan BS et al., "CD8+ T cells and latent herpes simplex virus type 1: keeping the peace in sensory ganglia" *Expert Opinion on Biological Therapy*, 2007, 7(9):1323-1331, abstract only.
Shin-Ya M et al., "Intracellular interferon triggers Jak-Stat signaling cascade and induces p53-dependent antiviral protection" *Biochemical and Biophysical Research Communications*, 2005, 329(3):1139-1146.
Subramaniam PS and Johnson HM "The IFNAR1 subunit of the type I IFN receptor complex contains a functional nuclear localization sequence" *FEBS Letters*, 2004, 578:207-210.
Subramaniam PS and Johnson HM "Lipid Microdomains are Required Sites for the Selective Endocytosis and Nuclear Translocation of IFN-γ, Its Receptor Chain IFN-γ Receptor-1, and the Phosphorylation and Nuclear Translocation of STAT1α" *J. Immunology*, 2002, 169:1959-1969.
Subramaniam PS et al., "Differential recognition of the type I interferon receptor by interferons τ and α is responsible for their disparate cytotoxicities" *Proc. Natl. Acad. Sci. USA*, 1995, 92:12270-12274.
Szente BE et al., "Structural Requirements for Agonist Activity of a Murine Interferon-γ Peptide" *J. Interferon Cytokine Res.*, 1996, 16:813-817.
Szente BE et al. "Identification of IFN-γ Receptor Binding Sites for JAK2 and Enhancement of Binding by IFN-γ and Its C-Terminal Peptide IFN-γ(95-133)" *J. Immunology*, 1995, 155:5617-5622.
Szretter KJ et al., "Early Control of H5N1 Influenza Virus Replication by the Type I Interferon Response in Mice" *Journal of Virology*, 2009, 83(11):5825-5834.
Waiboci LW et al., "Both the Suppressor of Cytokine Signaling 1 (SOCS-1) Kinase Inhibitory Region and SOCS-1 Mimetic Bind to JAK2 Autophosphorylation Site: Implications for the Development of a SOCS-1 Antagonist" *The Journal of Immunology*, 2007, 178:5058-5068.
Wald A and Link K "Risk of Human Immunodeficiency Virus Infection in Herpes Simplex Virus Type 2-Seropositive Persons: A Meta-Analysis" *The Journal of Infectious Diseases*, 2002, 185(1):45-52.
Wei L et al., "Discrete Roles of STAT4 and STAT6 Transcription Factors in Tuning Epigenetic Modifications and Transcription during T Helper Cell Differentiation" *Immunity*, 2010, 32:840-851.
Yang XP et al., "Opposing regulation of the locus encoding IL-17 through direct, reciprocal actions of STAT3 and STAT5" *Nature Immunology*, 2011, 12:247-254.
Yasukawa H et al., "The JAK-binding protein JAB inhibits Janus tyrosine kinase activity through binding in the activation loop" *The EMBO Journal*, 1999, 18(5):1309-1320.
Yokota SI et al., "Induction of Suppressor of Cytokine Signaling-3 by Herpes Simplex Virus Type 1 Contributes to Inhibition of Interferon Signaling Pathway" *Journal of Virology*, 2004, 78(12):6282-6286.
Yoshimura, A et al., "SOCS proteins, cytokine signalling and immune regulation" *Nature Reviews*, 2007, 7:454-465.
Zouein FA et al., "JAKs go nuclear: Emerging role of nuclear JAK1 and JAK2 in gene expression and cell growth" *Growth Factors*, 2011, 29(6):245-252.
Ahmed, C. and Johnson, H. "Short Peptide Type I Interferon Mimetics: Therapeutics for Experimental Allergic Encephalomyelitis, Melanoma, and Viral Infections" *J. Interferon & Cytokine Res.*, 2014, 34(10):802-809.

* cited by examiner

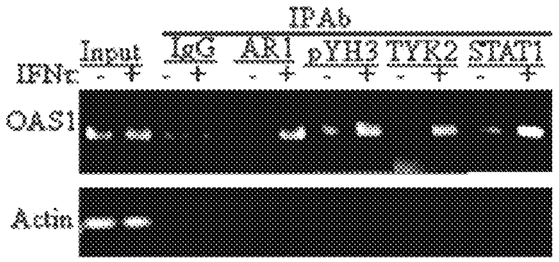
FIG. 3
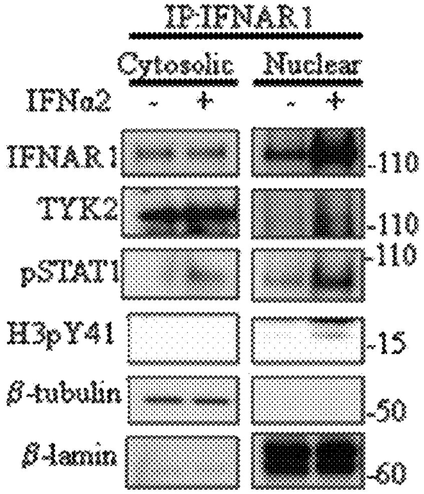
FIG. 4
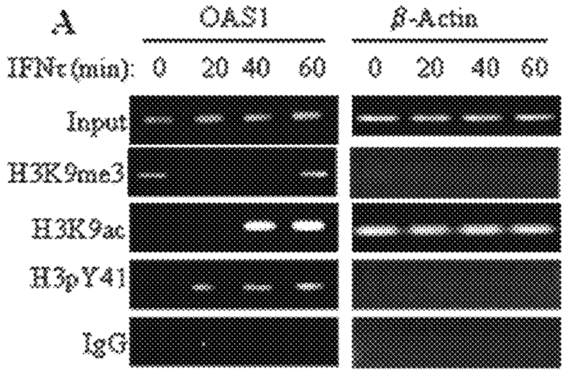
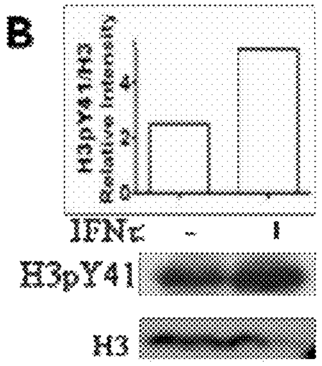
FIG. 5A
FIG. 5B

TYPE I INTERFERON MIMETICS AS THERAPEUTICS FOR CANCER, VIRAL INFECTIONS, AND MULTIPLE SCLEROSIS

CROSS-REFERENCE TO RELATED APPLICATIONS

The present application is a continuation-in-part of International Application No. PCT/US2012/043565, filed Jun. 21, 2012, which claims the benefit of U.S. Provisional Application Ser. No. 61/499,495, filed Jun. 21, 2011, each of which is hereby incorporated by reference herein in its entirety, including any figures, tables, nucleic acid sequences, amino acid sequences, or drawings.

GOVERNMENT SUPPORT

This invention was made with government support under grant number R01 AI056152 awarded by the National Institutes of Health. The government has certain rights in the invention.

The Sequence Listing for this application is labeled "2FD4338.TXT" which was created on Jul. 8, 2015 and is 21 KB. The entire contents of the sequence listing is incorporated herein by reference in its entirety.

BACKGROUND OF THE INVENTION

Viruses are a heterogeneous group of intracellular infectious agents that depend in varying degrees on the host synthetic machinery for replication. The poxviruses are large, double-stranded DNA viruses that are assembled in the cytoplasm of infected cells involving complex replication mechanisms (Moss, 2007). Attachment, internalization, and disassembling of poxviruses precedes the initiation of three waves of mRNA synthesis. The early wave codes for virus growth factors and decoy cytokine receptors. Decoy receptors for both type I and type II interferons (IFNs) are produced during early protein synthesis in poxvirus infected cells, thus blunting perhaps the most important innate host defense system against viral infections (Moss and Shisler, 2001). A well-known example of this is the B8R protein of vaccinia virus, which is a homolog of the extracellular domain of the IFNγ receptor (Moss, 2007).

Encephalomyocarditis (EMC) virus is a small single-stranded RNA picornavirus of the plus strand orientation with wide host range (Racaniello, 2007). In mice, EMC virus infection is lethal, but is quite susceptible to IFNγ or an IFNγ mimetic treatment at early stages of infection (Mujtaba et al., 2006). The IFNγ mimetic is also effective against vaccinia virus infection even in the presence of B8R decoy receptor (Ahmed et al., 2005; Ahmed et al., 2007). The IFNγ mimetic is a small peptide corresponding to the C-terminus of IFNγ that functions intracellularly and thus does not interact with the extracellular domain of the IFNγ receptor (Ahmed et al., 2005).

The IFNγ mimetic is also effective against another large double-stranded DNA virus called herpes simplex 1 or HSV-1 that replicates in the cell nucleus (Frey et al., 2009). Close relatives include the herpes Zoster virus and cytomegalovirus (Roizman et al., 2007). The broad spectrum of antiviral activity of IFNγ mimetics is unique in that we are unaware of any other small antiviral that exhibits strong activity against poxviruses, picornaviruses, and herpes viruses.

The IFN system is regulated by an inducible endogenous tyrosine kinase inhibitor called suppressor of cytokine signaling 1 or SOCS-1 (Yoshimura et al., 2007; Mansell et al., 2006; Yasukawa et al., 1999; Kobayashi et al., 2006; Croker et al., 2008). SOCS-1 is a member of a family of inducible proteins that negatively regulate IFN and other cytokine signaling via inhibition of JAK/STAT signaling (Yoshimura et al., 2007). There are currently eight members of the SOCS family, SOCS-1 to SOCS-7 and cytokine-inducible SH2 protein. SOCS-1 has distinct regions or domains that define the mechanism by which it inhibits the function of JAK tyrosine kinases such as JAK2 that are involved in activation of STAT transcription factors (Yoshimura et al., 2007). The N-terminus of SOCS-1 contains a SH2 domain, and N-terminal to it is an extended SH2 sequence (ESS) adjacent to a kinase inhibitory region (KIR) (Yoshimura et al., 2007). These domains or regions of SOCS-1 bind to the activation and catalytic regions of JAK2 and block its function. The C-terminus of SOCS-1 contains a domain called the SOCS box, which is involved in proteasomal degradation of JAK2. It has been shown that the KIR sequence of SOCS-1 binds to a peptide corresponding to the activation loop of JAK2, pJAK2(1001-1013), and that the peptide pJAK2(1001-1013) blocked SOCS-1 activity in cells (Waiboci et al., 2007). Specifically, pJAK2(1001-1013) enhances suboptimal IFN activity, blocks SOCS-1 induced inhibition of STAT3 activation, enhances IFNγ activation site promoter activity, and enhances antigen-specific proliferation.

Influenza A virus is a segmented negative strand RNA virus that is responsible for over 30,000 deaths annually in the United States (Palese and Shaw, 2007). Pandemic influenza A virus infection can cause the deaths of millions world-wide. Type I IFNs are an important early innate immune response cytokine against influenza respiratory infections (Szretter et al., 2009). Influenza virus-encoded nonstructural protein NS1 is multifunctional and is important in virus defense against IFNs by a mechanism(s) that is not fully understood but may involve induction of SOCS-1 and SOCS-3, which in turn would negatively regulate IFN signaling (Pothlichet et al., 2008).

Herpes Simplex Virus (HSV) is a member of a broad class of double-stranded DNA viruses that undergo replication in the cell nucleus. Examples of other members are varicella-zoster virus (VZV) and cytomegalovirus (CMV) (Roizman et al., 2007). It is estimated that HSV-1 infects 60 to 80 percent of the people throughout the world, and persists for life in the infected individuals (Diefenbach et al., 2008; Koelle and Corey, 2008; Cunningham et al., 2006). Primary infection commonly occurs through cells of the mucous membrane and is often asymptomatic. This is followed by uptake of virus by sensory nerve fibers and retrograde transport to the cell body of the neurons in the dorsal root or trigeminal ganglion. Here, acute infection is converted to latency and from which HSV-1 periodically migrates down the nerve tissue to again infect mucosal cells for overt disease (Roizman et al., 2007; Diefenbach et al., 2008; Koelle and Corey, 2008; Cunningham et al., 2006).

HSV-1 infection is characterized by a strong cytokine response in infected cells, particularly the induction of type I IFNs (Cunningham et al., 2006). Infection of keratinocytes, for example, results in induction of large amounts of IFNα and IFNβ as well as interleukins 1, 6, and β-chemokines (Mikloska et al., 1998). IFNs, macrophages, natural killer (NK) cells, and gamma/delta T cells all play an important role in host innate immune response to HSV-1 (Cunningham et al., 2006). Toll-like receptor (TLR) 2 is activated on the cell surface by HSV-1, while TLR-9 is activated intracellularly by viral DNA. The latter stimulus is thought to play an important role in induction of IFNα by HSV-1 (Cunningham et al., 2006).

The adaptive immune response plays an important role in confining HSV-1 and other herpes virus infections to a latent state where $CD8^+$ T cells and IFNγ play critical roles (Knickelbein et al., 2008; Sheridan et al., 2007; Decman et al., 2005). It is functionally connected to the innate immune system where NK cells can serve as a source of IFNγ, which is also produced by $CD4^+$ and CD $8^+$ T cells. IFNγ can exert direct antiviral activity as well as induce upregulation of MHC class I and class II molecules on macrophages, dendritic cells, and keratinocytes (Decman et al., 2005). Direct effects of IFNγ as per a mouse model suggest that this IFN prevents reactivation of HSV by inhibition of function of the key intermediate protein ICP0 (Mossman, 2005). Interaction of the antigen presenting cells with $CD4^+$ T cells induces $CD8^+$ T cells to control HSV-1 levels in mucosal lesions (Arduino and Porter, 2008; Patel et al., 2007).

HSV-1 has developed several mechanisms to inhibit both the innate and adaptive immune responses to infection. HSV-1 downregulation of class I MHC expression occurs through high affinity binding of viral immediate early gene product ICP47 to the transporter associated with antigen processing (TAP) (Burgos et al., 2006), which blocks IFNγ induction of cytotoxic $CD8^+$ T cells (Goldsmith et al., 1998). IFN signaling is also inhibited by blockage of JAK/STAT transcription factor phosphorylation by an unknown mechanism (Chee and Roizman, 2004). ICP0 is thought to enhance proteasome-dependent degradation of IFN stimulated genes (ISGs) (Halford et al., 2006; Edison et al., 2002). A recent study suggests that HSV-1 can exert an anti-interferon effect by activation of a protein called suppressor of cytokine signaling 3 (SOCS-3) (Yokota et al., 2004).

Currently, there are no effective therapeutics available against HSV infection, except the nucleoside analog acyclovir (Dorsky and Crumpacker, 1987), which is known to have serious side effects. A search for a vaccine against HSV has remained elusive because of the successful adaptation to the host used by HSV (Koelle and Corey, 2008). Along with direct effects, infection with HSV has been found to increase the incidence of HIV infection, probably due to HSV-associated lesions (Wald and Link, 2002). Because of this interplay between HSV and HIV, it is conceivable that anti-HSV treatment may reduce the incidence of infection with HIV.

Type I interferons (IFNs), IFNα and IFNβ have been clinically approved for the treatment of hairy cell leukemia, chronic myelogenous leukemia, melanoma, hepatitis C virus infection, and multiple sclerosis. Treatment with these IFNs is associated with severe side effects, including bone marrow suppression, depression, and fever, which has resulted in several patients dropping out of treatment programs. There remains a need in the art for type I IFN mimetics that can provide the same benefits as the parent interferons, while having less of the undesirable effects.

The classical model of cytokine signaling dominates our view of specific gene activation by cytokines such as the interferons (IFNs) (Levy and Darnell, 2002). In this model, ligand activates the cell solely via interaction with the extracellular domain of the receptor complex. This in turn results in the activation of receptor or receptor-associated tyrosine kinases, primarily of the Janus or JAK kinase family, leading to phosphorylation and dimerization of the STAT transcription factors, which then disassociate from the receptor cytoplasmic domain and translocate to the nucleus. This view ascribes no further role to the ligand, JAKs, or the receptor in the signaling process. Further, there is the suggestion that the STAT transcription factors possess intrinsic nuclear localization sequences (NLSs) that are responsible for nuclear translocation of STATs and specific gene activation (McBride et al., 2000; Melen et al., 2001; Begitt et al., 2000).

It has recently been acknowledged that the classical model of JAK/STAT signaling was over-simplified in its original form. In the case of IFNγ, complexity beyond simple JAK/STAT activation is indicated in the relatively recent demonstration that other pathways, including MAP kinase, PI3 kinase, CaM kinase II, NF-κB, and others cooperate with or act in parallel to JAK/STAT signaling to regulate IFNγ effects at the level of gene activation and cell phenotypes (Gough et al., 2008). All of these pathways are generic in the sense that a plethora of cytokines with functions different from those of IFNγ also activate them. Thus, uniqueness of function would seem to depend on cytokine control of complex and unique qualitative, quantitative, and kinetic aspects of activation of these pathways. This uniqueness has thus far not been demonstrated.

At the STAT level, there is evidence of a functional interaction between different STATs in gene activation/suppression, which provides more insight into STAT mediation of cytokine signaling. The induction of IL-17 by activated STAT3, for example, was countered by IL-2 activation of STAT5 (Yang et al., 2011). It was demonstrated by chromatin immunoprecipitation (ChIP) sequencing that STAT3 and STAT5 bound to multiple common sites across the IL-17 gene locus, including non-coding sequences. The activation state of these STATs was not addressed. Induction of STAT5 by IL-2 resulted in more binding of STAT5 and less binding of STAT3 at these sites, whereas induction of STAT3 by IL-6 induced the opposite; the combination of the two STATs resulted in dynamic regulation of the IL-17 gene locus by the opposing effects of IL-2 (STAT5) and IL-6 (STAT3) (Yang et al., 2011). A similar complementarity was observed with STAT4 and STAT6 with respect to Th1 and Th2 cell development, but with much less competition for binding sites at coding and non-coding regions of the gene (Wei et al., 2010). These Yin-Yang interactions of STAT transcriptions factors are referred to as specification with respect to lymphocyte phenotypes. It is not clear, however, as to how these STAT interactions at the level of DNA binding translate into specific gene activation by the inducing cytokine.

There is evidence that JAK kinases, including the mutant JAK2V617F, play an important role in the epigenetics of gene activation in addition to STAT activation in the cytoplasm (Dawson et al., 2009). Leukemic cells with a JAK2V617F gain-of-function mutation have constitutively active JAK2V617F in the nucleus. This leads to phosphorylation of Y41 on histone H3, which results in disassociation of heterochromatin protein 1α, HP1α. The heterochromatin remodeling was associated with exposure of euchromatin for gene activation. Although present in the nucleus, wild-type JAK2 was only activated when K562 cells were treated with PDGF or LIF, or when BaF3 cells were treated with IL-3. The question of how a ligand/receptor interaction resulted in the presence of activated JAK2, pJAK2, in the nucleus was not addressed, nor its targeting mechanism to discrete genomic sites and specific promoters.

It has been shown in the case of IFNγ that receptor subunit IFNGR1 is associated with pJAK2 and phosphorylated histone H3Y41 at the promoter of the IRF1 gene, while the β-actin gene is unaffected, since it is not acted on by IFNγ

(Noon-Song et al., 2011). Activated TYK2, pTYK2, in the nucleus and at promoters of genes activated by type I IFNs. TYK2 is also activated by other cytokines such as IL-12 and IL-23, which have biological effects different from IFN (Jones and Vignali, 2011; Duvallet et al., 2011). We were therefore particularly interested in whether there was an association between pTYK2 and type I IFN receptors at the promoters and chromatin of genes activated by these IFNs and whether such association provided insight into pTYK2 induced specific epigenetic events in genes activated by the IFNs. The findings provide insight into the mechanism of specific gene activation by type I IFNs, including the associated epigenetic events.

BRIEF SUMMARY OF THE INVENTION

The subject invention pertains to agonist peptides of type I interferons and methods of using the peptides. These peptides are based on the amino acid sequence of the C-terminus region of the type I IFN molecules and are capable of binding to the cytoplasmic domain of type I IFN receptors. Surprisingly, these peptides were found to possess the same or similar biological activity as that associated with the full-length, mature type I IFN proteins, even though these peptides do not bind to the extracellular domain of the type I IFN receptors. In one embodiment, the peptide is a peptide of IFNα. In another embodiment, the peptide is a peptide of IFNβ. The subject peptides have been shown to effect increased resistance to viral infection. Peptides of the invention can be used to treat or prevent viral infections, to treat oncological disorders, and to treat autoimmune disorders, such as multiple sclerosis.

BRIEF DESCRIPTION OF THE DRAWINGS

(FIG. 1C) WISH cells were similarly treated with IFNτ and the nuclear fraction was Western blotted with antibodies to IFNAR2 and IFNAR1.-tubulin (cytoplasm) and -lamin (nucleus) blots were performed to confirm the purity of nuclear fraction.

FIG. 3. Type I IFN stimulation induces the association of IFNAR1, TYK2, STAT1α, and H3pY41 with the ISRE at the OAS1 promoter by ChIP assay. WISH cells were treated with 1,000 U/ml of IFNτ for 1 hr, then treated with 1% formaldehyde for 10 min. Details of ChIP assay are in MATERIALS and METHODS and described previously (Noon-Song et al., 2011). Abbrev: AR1, IFNAR1; pYH3, phosphorylated tyrosine 41 on histone H3.

FIG. 4. Association of TYK2, pSTAT1α, and H3pY41 with IFNAR1 in the nucleus of cells treated with a type I IFN. WISH cells were treated with 1,000 U/ml of IFNα2 for 1 hr, after which a solubilized extract from the isolated nuclei was immunoprecipitated with antibodies to IFNAR1 and Western blotted with the indicated antibodies (see MATERIALS and METHODS).

FIGS. 5A-5B. Type I IFN treatment induces histone H3K9 demethylation/acetylation as well as H3Y41 phosphorylation at the ISRE of the promoter region of the OAS1 gene. (FIG. 5A) WISH cells were treated with 1,000 U/ml of IFNτ for the indicated time and ChIP assays were performed as in FIG. 3 using antibodies to H3K9ac, H3K9me3, and H3pY41. (FIG. 5B) Western blot for H3pY41 in WISH cells treated with IFNτ as indicated in FIG. 5A. Abbrev: H3K9ac, acetylated lysine 9 in histone H3; H3pY41, phosphorylated tyrosine 41 in histone H3; H3K9me3, trimethylated lysine 9 in histone H3.

(FIG. 6C) SJL/J mice (n=5), were injected i.p. with PBS (●), IFNα mimetic, IFNα1(69-189)R9 (▲, 15 μg/mouse), or the control peptide, IFNα1(69-189) (□, 15 μg/mouse), every other day starting from day 12 post-immunization with MBP. Mice were followed daily. The mean daily severity of disease was graded as follows. 0, normal; 1, loss of tail tone; 2, hind leg weakness; 3, paraparesis; 4, paraplegia; 5, moribund; and 6, death.

BRIEF DESCRIPTION OF THE SEQUENCES

Figures 1A, 1B, 1C:
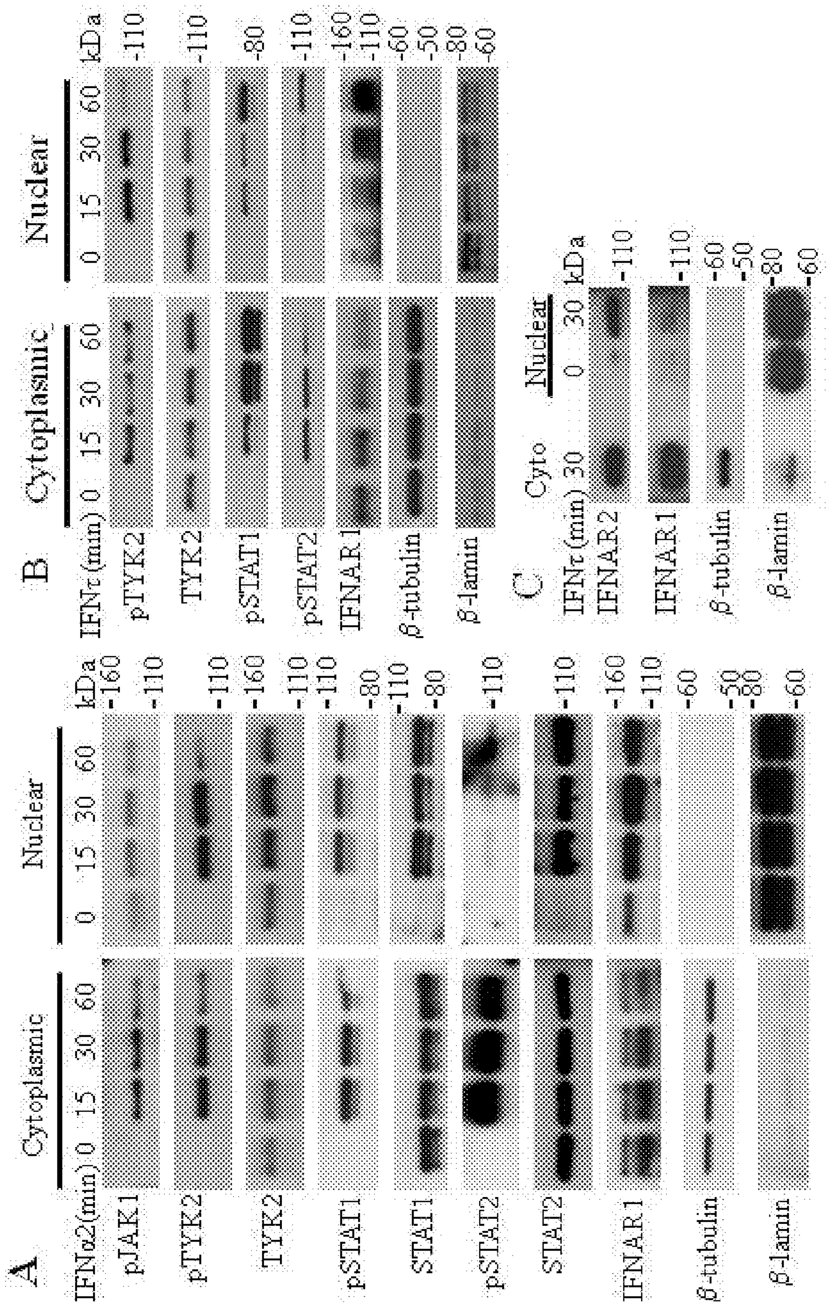
FIGS. 1A-1C. Activated JAKs and receptor subunits are present in the nucleus of cells treated with type I IFNs. WISH cells were incubated with or without 1,000 U/ml of IFNα2 (FIG. 1A) or IFN (FIG. 1B) for the indicated times and their nuclei were purified and solubilized (see MATERIALS and METHODS). Nuclear and cytoplasmic samples were subjected to Western blotting against indicated antibodies.

SEQ ID NO:1 is a peptide mimetic of human IFNα1.

SEQ ID NO:2 is a peptide mimetic of human IFNβ1.

SEQ ID NO:3 is a peptide mimetic of SEQ ID NO:1 that further comprises a lipophilic sequence on the N-terminus of the peptide.

SEQ ID NO:4 is a peptide mimetic of SEQ ID NO:2 that further comprises a lipophilic sequence on the N-terminus of the peptide.

SEQ ID NO:5 is a peptide mimetic of human IFNα2.

SEQ ID NO:6 is a peptide mimetic of human IFNα4.

SEQ ID NO:7 is the amino acid sequence of a peptide designated herein as MuIFNγ(95-132).

SEQ ID NO:8 is the amino acid sequence of a peptide designated herein as huIFNγ(95-134).

SEQ ID NO:9 is the amino acid sequence of a peptide designated herein as Tkip.

SEQ ID NO:10 is the amino acid sequence of a peptide designated herein as SOCS1-KIR.

SEQ ID NO:11 is the full-length precursor human IFNα1 amino acid sequence.

SEQ ID NO:12 is the full-length precursor human IFNβ1 amino acid sequence.

SEQ ID NO:13 is a histone H3 peptide.

SEQ ID NO:14 is a primer for amplifying human OAS1 promoter region.

SEQ ID NO:15 is a primer for amplifying human OAS1 promoter region.

SEQ ID NO:16 is a primer for amplifying human β-actin promoter region.

SEQ ID NO:17 is a primer for amplifying human β-actin promoter region.

SEQ ID NO:18 is a nuclear localization sequence of IFNAR2.

SEQ ID NOs:19-37 and 43 are cell-penetrating peptides that can be used in accordance with the subject invention.

SEQ ID NO:38 is a peptide mimetic of human lipo-IFNα1.

SEQ ID NO:39 is a peptide mimetic of human IFNβ.

SEQ ID NO:40 is a peptide mimetic of ovine lipo-IFNτ.

SEQ ID NO:41 is a peptide having a scrambled sequence of the lipo-IFNτ peptide.

SEQ ID NO:42 is the full-length ovine IFN-tau amino acid sequence.

DETAILED DESCRIPTION OF THE INVENTION

The subject invention pertains to agonist peptides of type I interferons and methods of using the peptides. These peptides are based on the amino acid sequence of the C-terminus region of the type I IFN molecules and are capable of binding to the cytoplasmic domain of type I IFN receptors and activating the receptor. Surprisingly, these peptides were found to possess the same or similar biological activity as that associated with the full-length, mature type I IFN proteins, even though these peptides do not bind to the extracellular domain of the type I IFN receptors. In one embodiment, the peptide is a peptide of IFNα protein (e.g., a human IFNα protein). In another embodiment, the peptide is a peptide of IFNβ protein (e.g., a human IFNβ protein). In a still further embodiment, the peptide is a peptide of an IFN-tau (IFNτ) protein. The subject peptides have been shown to provide for increased resistance to viral infection in cells and in animals. Peptides of the invention can be used to treat or prevent viral infections, to treat oncological disorders, and to treat autoimmune disorders, such as multiple sclerosis. Peptides of the invention generally lack the side effects associated with use of full-length type I IFNs.

In an exemplified embodiment, the huIFNα1 (69-189) peptide (SEQ ID NO:1) based on human IFNα1 has an amino acid sequence corresponding to amino acid residues 69 through 189 of the full-length human IFNα 1 protein (SEQ ID NO:11), or a fragment or variant thereof that retains substantially the same activity as the full-length non-variant peptide. In another embodiment, the huIFNα1 (152-189) peptide (SEQ ID NO:38) has an amino acid sequence corresponding to amino acid residues 152 through 189 of the full-length human IFNα1 protein, or a fragment or variant thereof that retains substantially the same activity as the full-length non-variant peptide. In a further embodiment, the huIFNβ1 (100-187) peptide (SEQ ID NO:2) based on human IFNβ1 has an amino acid sequence corresponding to amino acid residues 100 through 187 of the full-length human IFNβ1 protein (SEQ ID NO:12), or a fragment or variant thereof that retains substantially the same activity as the full-length non-variant peptide. In another embodiment, the huIFNβ1 (150-187) peptide (SEQ ID NO:39) has an amino acid sequence corresponding to amino acid residues 150 through 187 of the full-length human IFNβ1 protein, or a fragment or variant thereof that retains substantially the same activity as the full-length non-variant peptide. In another embodiment, the ovine IFNτ (156-195) peptide (SEQ ID NO:40) has an amino acid sequence corresponding to amino acid residues 156 through 195 of the full-length ovine IFNτ protein, or a fragment or variant thereof that retains substantially the same activity as the full-length non-variant peptide. In another embodiment, a peptide of the invention has the amino acid sequence shown in SEQ ID NO:5 or SEQ ID NO:6, or a fragment or variant thereof that retains substantially the same activity as the full-length non-variant peptide. Peptides of the invention can be provided in purified or isolated form.

In one embodiment, a peptide of the invention comprises a lipophilic sequence or moiety that facilitates penetration through a cell membrane for entry into a cell. In one embodiment, a peptide of the invention comprises one or more arginine or lysine amino acids at one or both termini of the peptide. In a specific embodiment, a peptide of the invention comprises one or more arginine amino acids at the N-terminus of the peptide. For example, a peptide can comprise 1, 2, 3, 4, 5, 6, 7, 8, 9, 10, or more arginine and/or lysine amino acids at one or both termini. In an exemplified embodiment, a peptide of the invention has the amino acid sequence shown in SEQ ID NO:3 or SEQ ID NO:4. In another embodiment, a peptide of the invention comprises a fatty acid moiety, e.g., a carboxylic acid with a long aliphatic tail, attached to the peptide. Examples of fatty acids contemplated within the scope of the invention include, but are not limited to, caprylic acid, capric acid, lauric acid, myristic acid, palmitic acid, stearic acid, arachidic acid, behenic acid, lignoceric acid, and cerotic acid. In a specific embodiment, a peptide of the invention comprises a palmitate or palmitic acid (hexadecanoic acid) attached to the peptide, typically at the N- and/or C-terminus of the peptide. In a further embodiment, a peptide of the invention comprises a nuclear localization sequence (NLS).

The discovery of peptide agonists of type I interferons is highly unexpected. Use of synthetic peptide agonists rather than the full-length type I IFN molecules offers advantages such as targeting of specific cells and immune system components. Also, specific amino acid residues of the peptides can be easily and rapidly modified to allow for generation of more effective agonists or antagonists.

As those skilled in the art can readily appreciate, there can be a number of variant sequences of a protein found in nature, in addition to those variants that can be artificially created by the skilled artisan in the lab. The peptides of the subject invention encompasses those specifically exemplified herein, as well as any natural variants thereof, as well as any variants which can be created artificially, so long as those variants retain the desired biological activity.

The peptides contemplated in the subject invention include the specific peptides exemplified herein as well as equivalent peptides which may be, for example, somewhat longer or shorter than the peptides exemplified herein. For example, using the teachings provided herein, a person skilled in the art could readily make peptides having from 1 to about 5, 10, 15, 20, 25, 30, 35, 40, 50, 60, 70 or more amino acids added to, or removed from, either end of the disclosed peptides using standard techniques known in the art. In one embodiment, amino acids are removed from the N-terminus of a peptide of the invention. In a specific embodiment, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70 or more amino acids can, independently, be removed from either or both ends of a peptide of the invention. Preferably, any added amino acids would be the same as the corresponding amino acids of a mature full-length type I IFN protein. The skilled artisan, having the benefit of the teachings disclosed in the subject application, could easily determine whether a variant peptide retained the biological activity of the specific peptides exemplified herein. Such a longer or shorter peptide would be within the scope of the subject invention as long as said peptide does not encompass the entire full-length IFN protein and said longer or shorter peptide retains substantially the same relevant biological activity as the peptides exemplified herein. For example, a longer or shorter variant of the huIFNα 1 (69-189) (SEQ ID NO:1) peptide would fall within the scope of the subject invention if the variant peptide had the ability to increase cellular resistance to viral infection.

Also within the scope of the subject invention are peptides which have the same amino acid sequences of a peptide exemplified herein except for amino acid substitutions, additions, or deletions within the sequence of the peptide, as long as these variant peptides retain substantially the same relevant biological activity as the peptides specifically exemplified herein. For example, conservative amino acid substitutions within a peptide which do not affect the ability of the peptide to, for example, to increase cellular resistance to viral infection would be within the scope of the subject invention. Thus, the peptides disclosed herein should be understood to include variants and fragments, as discussed above, of the specifically exemplified sequences.

The subject invention further includes nucleotide sequences which encode the peptides disclosed herein. These nucleotide sequences can be readily constructed by those skilled in the art having the knowledge of the protein and peptide amino acid sequences which are presented herein. As would be appreciated by one skilled in the art, the degeneracy of the genetic code enables the artisan to construct a variety of nucleotide sequences that encode a particular peptide or protein. The choice of a particular nucleotide sequence could depend, for example, upon the codon usage of a particular expression system.

The subject invention contemplates the use of the peptides described herein in pharmaceutical compositions for administration to an animal or human for the treatment of clinically important disease conditions that are amenable to treatment with a full-length interferon. For example, using the teachings described herein, the skilled artisan can use the subject invention to modulate or stimulate the immune response of an animal or human. Similarly, the subject peptides can be used to treat certain viral infections, as well as to treat certain forms of cancer or tumors. The peptides of the subject invention can be prepared in pharmaceutically acceptable carriers or diluents for administration to humans or animals in a physiologically tolerable form. Materials and methods for preparing such compositions are known in the art.

The peptides of the subject invention can be administered using a variety of techniques that are known in the art. The peptides can be encapsulated in liposomes that are targeted to specific cells or tissues and the liposome-encapsulated peptides delivered to the cells or tissue either in vitro, in vivo, or ex vivo. Procedures for preparing liposomes and encapsulating compounds within the liposome are well known in the art. See, for example, U.S. Pat. No. 5,252,348, which issued to Schreier et al. Peptides can also be conjugated or attached to other molecules, such as an antibody, that targeted a specific cell or tissue. Peptides can also be administered using a drug delivery system similar to that described in U.S. Pat. No. 4,625,014, which issued to Senter et al.

As described herein, the peptide sequences of the subject invention can also be the basis for producing peptides that act as type I IFN antagonists. These antagonists are also within the scope of the subject invention. Inhibition or antagonism of interferon function without agonist activity can be accomplished through the use of anti-peptide antibodies or modification of residues within the peptide itself. An especially productive means for generation of peptide antagonists has been substitution of L-amino acids with D-amino acids. The efficacy of this approach has been well characterized in the generation of arginine vasopressin analogs with selectively enhanced antidiuretic antagonism by appropriate substitution of L-amino acids with D-amino acids (Manning et al., 1985). Further, not only can antagonism be produced with D-amino acid substitutions, but this antagonism can be directed toward a specific function. Production of potent antagonist peptides can be of value in specifically manipulating immune function.

A further aspect of the claimed invention is the use of the claimed peptides to produce antibodies, both polyclonal and monoclonal. These antibodies can be produced using standard procedures well known to those skilled in the art. These antibodies may be used as diagnostic and therapeutic reagents. For example, antibodies that bind to the human IFNα1(69-189) (SEQ ID NO:1) or IFNα1(152-189) (SEQ ID NO:38) peptide can be used as an antagonist to block the function of IFNα. Similarly, antibodies that bind to human IFNβ1(100-187) (SEQ ID NO:2) or IFNβ1(150-187) (SEQ ID NO:39) peptide can be used as an antagonist to block the function of IFNβ. Antibodies that bind to ovine IFNτ(156-195) (SEQ ID NO:40) peptide can be used as an antagonist to block the function of IFNτ. Antibodies that are reactive with the peptides of the subject invention can also be used to purify type I IFN protein or peptides from a crude mixture. In one embodiment, an antibody binds specifically to the human IFNα1(69-189) (SEQ ID NO:1) or IFNα1 (152-189) (SEQ ID NO:38) peptide. In another embodiment, an antibody binds specifically to the human IFNβ1(100-187) (SEQ ID NO:2) or IFNβ1(150-187) (SEQ ID NO:39) peptide.

An antibody that is contemplated by the present invention can be in any of a variety of forms, including a whole immunoglobulin, an antibody fragment such as Fv, Fab, and similar fragments, as well as a single chain antibody that includes the variable domain complementarity determining regions (CDR), and similar forms, all of which fall under the broad term "antibody," as used herein.

The term "antibody fragment" refers to a portion of a full-length antibody, generally the antigen binding or variable region. Examples of antibody fragments include Fab, Fab', $F(ab')_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment of an antibody yields an $F(ab')_2$ fragment that has two antigen binding fragments, which are capable of cross-linking antigen, and a residual other fragment (which is termed pFc'). Additional fragments can include diabodies, linear antibodies, single-chain antibody molecules, and multispecific antibodies formed from antibody fragments. As used herein, "antigen binding fragment" with respect to antibodies, refers to, for example, Fv, F(ab) and $F(ab')_2$ fragments.

Antibody fragments can retain an ability to selectively bind with the antigen or analyte are contemplated within the scope of the invention and include:

(1) Fab is the fragment of an antibody that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) $(Fab')_2$ is the fragment of an antibody that can be obtained by treating whole antibody with the enzyme pepsin without subsequent reduction. $F(ab')_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain ($V_L$), the variable region of the heavy chain ($V_H$), linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the $V_H$ and $V_L$ domains that enables the sFv to form the desired structure for antigen binding. For a review of sFv fragments, see Pluckthun in The Pharmacology of Monoclonal Antibodies, vol. 113, Rosenburg and Moore eds. Springer-Verlag, N.Y., pp. 269 315 (1994).

Antibodies within the scope of the invention can be of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes.

Antibodies of the subject invention can be genus or species specific to a target. Antibodies of the invention can be prepared using standard techniques known in the art. Antibodies useful in the invention can be polyclonal or monoclonal antibodies. Monoclonal antibodies can be prepared using standard methods known in the art (Kohler et al., 1975). Antibodies of the invention can be mammalian antibodies, including mouse, rat, goat, rabbit, pig, dog, cat, monkey, chimpanzee, ape, or human.

The subject peptides can also be used in the design of new drugs that bind to the cytoplasmic domain of a type I IFN receptor. Knowledge of peptide sequences that induce type I IFN biological activity upon binding of the peptide to a localized region on the type I IFN receptor enables a skilled artisan to develop additional bioactive compounds using rational drug design techniques. Thus, the skilled artisan can prepare both agonist and antagonist drugs using the teachings described herein.

The subject invention also concerns compositions comprising one or more peptides or polynucleotides of the invention. In one embodiment, a composition further comprises a suitable carrier, diluent, or buffer. Compositions contemplated within the scope of the invention can comprise one or more peptides or polynucleotides of the invention and, optionally, one or more other antiviral compounds. For example, a peptide of the invention can be provided in a composition with one or more of IFNα, IFNβ, IFNγ, acyclovir (ZOVIRAX), zidovudine (ZDV) (RETROVIR), lamivudine (3TC) (EPIVIR), zanamivir (RELENZA), oseltamivir (TAMIELU), valacyclovir (VALTREX), amantadine (SYMMETREL), rimantadine (FLUMADINE), cidofovir (VISTIDE), foscarnet (FOSCAVIR), ganciclovir (CYTOVENE), ribavirin (VIRAZOLE), nelfinavir (VIRACEPT), ritonavir (NORVIR), rifampin (RIFADIN), and famciclovir (FAMVIR). In one embodiment, the composition comprises a peptide or polynucleotide of the invention in a pharmaceutically or physiologically acceptable carrier, buffer, or diluent. Compositions of the invention can comprise additional peptides such as an IFNγ mimetic. Examples of IFNγ mimetic peptides are described in U.S. Pat. Nos. 5,770,191 and 6,120,762. In one embodiment, the IFNγ mimetic peptide comprises the amino acid sequence shown in SEQ ID NO:7 (MuIFNγ(95-132)) or SEQ ID NO:8 (huIFNγ(95-134)), or a fragment or variant thereof that exhibits antiviral activity. In one embodiment, a composition of the invention can comprise one or more peptides comprising the amino acid sequence shown in SEQ ID NO:9 (Tkip peptide), or a fragment or variant thereof that exhibits antiviral activity, and/or a peptide comprising the amino acid sequence shown in SEQ ID NO:10 (SOCS1-KIR), or a fragment or variant thereof that exhibits antiviral activity.

The methods of the invention contemplate that a peptide, polynucleotide, composition, or other agent of the invention is administered to the person or animal prior to infection by a virus. Also contemplated within the scope of the methods is that a peptide, polynucleotide, composition, or other agent of the invention is administered at the time of infection or after the person or animal has been infected. In one embodiment, a person or animal to be treated is one that has previously been vaccinated against infection by a virus, such as a poxvirus. In another embodiment, the person or animal has not been previously vaccinated against the virus.

In one embodiment, peptides, polynucleotides, antibodies, and other agents of the invention are modified so as to enhance uptake into a cell. In one embodiment, a lipophilic group is attached to a peptide, polynucleotide, or other agent of the invention. In one embodiment, a palmitic acid is attached to a peptide of the invention. In a specific embodiment, a palmitoyl-lysine group is attached to the peptide, for example at the N-terminus of the peptide. Other methods for enhancing uptake of a peptide, polynucleotide, and antibody into a cell are known in the art and are contemplated within the scope of the invention.

Peptides, polynucleotides, antibodies, compositions, and other agents of the invention can also be delivered into cells by encapsulation of the peptide, polynucleotide, antibody, and other agents of the invention within a liposome. Methods for encapsulation of peptides, polynucleotides, antibodies, and other agents of the invention within liposomes are well known in the art.

Peptides having substitution of amino acids other than those specifically exemplified in the subject peptides are also contemplated within the scope of the present invention. For example, non-natural amino acids can be substituted for the amino acids of a peptide of the invention, so long as the peptide having substituted amino acids retains substantially the same activity as the peptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ϵ-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

Amino acids can be generally categorized in the following classes: non-polar, uncharged polar, basic, and acidic. Conservative substitutions whereby a peptide having an amino acid of one class is replaced with another amino acid of the same class fall within the scope of the subject invention so long as the peptide having the substitution still retains substantially the same biological activity as a peptide that does not have the substitution. Table 1 below provides a listing of examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Single letter amino acid abbreviations are defined in Table 2.

TABLE 2

| Letter Symbol | Amino Acid |
|---|---|
| A | Alanine |
| B | Asparagine or aspartic acid |
| C | Cysteine |
| D | Aspartic Acid |
| E | Glutamic Acid |
| F | Phenylalanine |
| G | Glycine |
| H | Histidine |
| I | Isoleucine |
| K | Lysine |
| L | Leucine |
| M | Methionine |
| N | Asparagine |
| P | Proline |
| Q | Glutamine |
| R | Arginine |
| S | Serine |
| T | Threonine |
| V | Valine |
| W | Tryptophan |
| Y | Tyrosine |
| Z | Glutamine or glutamic acid |

The peptides of the present invention can be formulated into pharmaceutically-acceptable salt forms. Pharmaceutically-acceptable salt forms include the acid addition salts and include hydrochloric, hydrobromic, nitric, phosphoric, carbonic, sulphuric, and organic acids like acetic, propionic, benzoic, succinic, fumaric, mandelic, oxalic, citric, tartaric, maleic, and the like. Pharmaceutically-acceptable base addition salts include sodium, potassium, calcium, ammonium, and magnesium salts. Pharmaceutically-acceptable salts of the peptides of the invention can be prepared using conventional techniques.

The subject invention also concerns polynucleotide expression constructs that comprise a polynucleotide of the present invention comprising a nucleotide sequence encoding a peptide of the present invention. In one embodiment, the polynucleotide encodes a peptide comprising the amino acid sequence shown in SEQ ID NO:1, SEQ ID NO:2, SEQ ID NO:3, SEQ ID NO:4, SEQ ID NO:5, SEQ ID NO:6, SEQ ID NO:38, SEQ ID NO:39, or SEQ ID NO:40, or a fragment or variant thereof that exhibits substantially the same activity as the full-length non-variant peptide.

As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

Expression constructs of the invention will also generally include regulatory elements that are functional in the intended host cell in which the expression construct is to be expressed. Thus, a person of ordinary skill in the art can select regulatory elements for use in, for example, bacterial host cells, yeast host cells, plant host cells, insect host cells, mammalian host cells, and human host cells. Regulatory elements include promoters, transcription termination sequences, translation termination sequences, enhancers, and polyadenylation elements.

An expression construct of the invention can comprise a promoter sequence operably linked to a polynucleotide sequence encoding a peptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

For expression in animal cells, an expression construct of the invention can comprise suitable promoters that can drive transcription of the polynucleotide sequence. If the cells are mammalian cells, then promoters such as, for example, actin promoter, metallothionein promoter, NF-kappaB promoter, EGR promoter, SRE promoter, IL-2 promoter, NFAT promoter, osteocalcin promoter, SV40 early promoter and SV40 late promoter, Lck promoter, BMP5 promoter, TRP-1 promoter, murine mammary tumor virus long terminal repeat promoter, STAT promoter, or an immunoglobulin promoter can be used in the expression construct. The baculovirus polyhedrin promoter can be used with an expression construct of the invention for expression in insect cells. Promoters suitable for use with an expression construct of the invention in yeast cells include, but are not limited to, 3-phosphoglycerate kinase promoter, glyceraldehyde-3-phosphate dehydrogenase promoter, metallothionein promoter, alcohol dehydrogenase-2 promoter, and hexokinase promoter.

For expression in prokaryotic systems, an expression construct of the invention can comprise promoters such as, for example, alkaline phosphatase promoter, tryptophan (trp) promoter, lambda $P_L$ promoter, β-lactamase promoter, lactose promoter, phoA promoter, T3 promoter, T7 promoter, or tac promoter (de Boer et al., 1983).

If the expression construct is to be provided in a plant cell, plant viral promoters, such as, for example, the cauliflower mosaic virus (CaMV) 35S (including the enhanced CaMV 35S promoter (see, for example U.S. Pat. No. 5,106,739)) or 19S promoter can be used. Plant promoters such as prolifera promoter, Ap3 promoter, heat shock promoters, T-DNA 1'- or 2'-promoter of *A. tumafaciens*, polygalacturonase promoter, chalcone synthase A (CHS-A) promoter from petunia, tobacco PR-1a promoter, ubiquitin promoter, actin promoter, alcA gene promoter, pin2 promoter (Xu et al., 1993), maize WipI promoter, maize trpA gene promoter (U.S. Pat. No. 5,625,136), maize CDPK gene promoter, and RUBISCO SSU promoter (U.S. Pat. No. 5,034,322) can also be used. Seed-specific promoters such as the promoter from a β-phaseolin gene (of kidney bean) or a glycinin gene (of soybean), and others, can also be used. Constitutive promoters (such as the CaMV, ubiquitin, actin, or NOS promoter), tissue-specific promoters (such as the E8 promoter from tomato), developmentally-regulated promoters, and inducible promoters (such as those promoters than can be induced by heat, light, hormones, or chemicals) are contemplated for use with the polynucleotides of the invention.

Expression constructs of the invention may optionally contain a transcription termination sequence, a translation termination sequence, signal peptide sequence, and/or enhancer elements. Transcription termination regions can typically be obtained from the 3' untranslated region of a eukaryotic or viral gene sequence. Transcription termination sequences can be positioned downstream of a coding sequence to provide for efficient termination. Signal peptides are a group of short amino terminal sequences that encode information responsible for the relocation of an operably linked peptide to a wide range of post-translational cellular destinations, ranging from a specific organelle compartment to sites of protein action and the extracellular environment. Targeting a peptide to an intended cellular and/or extracellular destination through the use of operably linked signal peptide sequence is contemplated for use with the peptides of the invention. Chemical enhancers are cis-acting elements that increase gene transcription and can also be included in the expression construct. Chemical enhancer elements are known in the art, and include, but are not limited to, the CaMV 35S enhancer element, cytomegalovirus (CMV) early promoter enhancer element, and the SV40 enhancer element. DNA sequences which direct polyadenylation of the mRNA encoded by the structural gene can also be included in the expression construct.

Unique restriction enzyme sites can be included at the 5' and 3' ends of the expression construct to allow for insertion into a polynucleotide vector. As used herein, the term "vector" refers to any genetic element, including for example, plasmids, cosmids, chromosomes, phage, virus, and the like, which is capable of replication when associated with proper control elements and which can transfer polynucleotide sequences between cells. Vectors contain a nucleotide sequence that permits the vector to replicate in a selected host cell. A number of vectors are available for expression and/or cloning, and include, but are not limited to, pBR322, pUC series, M13 series, and pBLUESCRIPT vectors (Stratagene, La Jolla, Calif.).

Polynucleotides, vectors, and expression constructs of the subject invention can be introduced into a cell by methods known in the art. Such methods include transfection, microinjection, electroporation, lipofection, cell fusion, calcium phosphate precipitation, and by biolistic methods. In one embodiment, a polynucleotide or expression construct of the invention can be introduced in vivo via a viral vector such as adeno-associated virus (AAV), herpes simplex virus (HSV), papillomavirus, adenovirus, and Epstein-Barr virus (EBV). Attenuated or defective forms of viral vectors that can be used with the subject invention are known in the art. Typically, defective virus is not capable of infection after the virus is introduced into a cell. Polynucleotides, vectors, and expression constructs of the invention can also be introduced in vivo via lipofection (DNA transfection via liposomes prepared from synthetic cationic lipids) (Felgner et al., 1987). Synthetic cationic lipids (LIPOFECTIN, Invitrogen Corp., La Jolla, Calif.) can be used to prepare liposomes to encapsulate a polynucleotide, vector, or expression construct of the invention. A polynucleotide, vector, or expression construct of the invention can also be introduced in vivo as naked DNA using methods known in the art, such as transfection, microinjection, electroporation, calcium phosphate precipitation, and by biolistic methods.

Polynucleotides and peptides of the subject invention can also be defined in terms of more particular identity and/or similarity ranges with those exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also contemplates those polynucleotide molecules (encoding peptides of the invention) having sequences which are sufficiently homologous with the polynucleotide sequences encoding a peptide of the invention so as to permit hybridization with that sequence under standard stringent conditions and standard methods (Maniatis, T. et al., 1982). As used herein, "stringent" conditions for hybridization refers to conditions wherein hybridization is typically carried out overnight at 20-25 C below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A. et al., 1983):

$$Tm=81.5C+16.6 \text{ Log } [Na+]+0.41(\% G+C)-0.61(\% \text{ formamide})-600/\text{length of duplex in base pairs.}$$

Washes are typically carried out as follows:

(1) Twice at room temperature for 15 minutes in 1×SSPE, 0.1% SDS (low stringency wash).

(2) Once at Tm-20 C for 15 minutes in 0.2×SSPE, 0.1% SDS (moderate stringency wash).

As used herein, the terms "nucleic acid" and "polynucleotide sequence" refer to a deoxyribonucleotide or ribonucleotide polymer in either single- or double-stranded form, and unless otherwise limited, would encompass known analogs of natural nucleotides that can function in a similar manner as naturally-occurring nucleotides. The polynucleotide sequences include both the DNA strand sequence that is transcribed into RNA and the RNA sequence that is translated into protein. The polynucleotide sequences include both full-length sequences as well as shorter sequences derived from the full-length sequences. It is understood that a particular polynucleotide sequence includes the degenerate codons of the native sequence or sequences which may be introduced to provide codon preference in a specific host cell. The polynucleotide sequences falling within the scope of the subject invention further include sequences which specifically hybridize with the sequences coding for a peptide of the invention. The polynucleotide includes both the sense and antisense strands as either individual strands or in the duplex.

The subject invention also concerns methods for inducing an antiviral state in a cell. In one embodiment, a cell is contacted with an effective amount of a peptide, polynucleotide, or a composition of the invention. In one embodiment, the cell is not infected with a virus prior to contact with a peptide, polynucleotide, or composition of the invention. In another embodiment, the cell is already infected with a virus prior to contact with a peptide, polynucleotide, or composition of the invention. In one embodiment, the peptide has the amino acid sequence of SEQ ID NO:1, SEQ ID NO:2, SEQ ID NO:3, SEQ ID NO:4, SEQ ID NO:5, SEQ ID NO:6, SEQ ID NO:38, SEQ ID NO:39, or SEQ ID NO:40, or a fragment or variant thereof that exhibits antiviral activity. In one embodiment, the composition comprises a peptide of the invention and an antiviral drug and/or a IFN mimetic. The cell can be a human or mammalian cell. In one embodiment, the cell can be a keratinocyte, a fibroblast, a macrophage, or a lymphocyte. Peptides, polynucleotides, compositions, and/or other agents of the invention can be delivered to a cell either through direct contact of peptide, etc. with the cell or via a carrier means. Carrier means for delivering compositions to cells are known in the art and include encapsulating the composition in a liposome moiety, and attaching the peptide or polynucleotide to a protein or nucleic acid that is targeted for delivery to the target cell. Published U.S. Patent Application Nos. 20030032594 and 20020120100 disclose amino acid sequences that can be coupled to another peptide, protein, or nucleic acid and that allows the peptide, protein, or nucleic acid to be translocated across biological membranes. Published U.S. Patent Application No. 20020035243 also describes compositions for transporting biological moieties, such as peptides and proteins across cell membranes for intracellular delivery. Peptides can also be delivered using a polynucleotide that encodes a subject peptide. In one embodiment, the polynucleotide is delivered to the cell where it is taken up and the polynucleotide is transcribed into RNA and the RNA is translated into the encoded peptide. Antiviral activity can be induced in a cell against viruses such as vaccinia virus, EMC virus, influenza virus, herpes simplex virus (e.g., HSV-1), cytomegalovirus, herpes zoster virus, and other herpes viruses, poxvirus, coxsackie virus, lentivirus (e.g., HIV), picornavirus and vesicular stomatitis virus (VSV). Methods of the invention can be conducted in vitro or in vivo.

The subject invention also concerns methods for preventing or treating a viral infection and/or a viral associated disorder in a patient. In one embodiment, the disorder is hepatitis (e.g., caused by hepatitis B or hepatitis C virus). In one embodiment, an effective amount of a peptide, polynucleotide, and/or composition of the present invention is administered to a patient having a viral infection and who is in need of treatment thereof. In another embodiment, the patient is not yet infected with a virus or does not yet have a viral associated disorder. Optionally, the patient is a person or animal at risk of virus infection or at risk of developing a viral associated disorder. In one embodiment, the peptide has the amino acid sequence in SEQ ID NO:1, SEQ ID NO:2, SEQ ID NO:3, SEQ ID NO:4, SEQ ID NO:5, SEQ ID NO:6, SEQ ID NO:38, SEQ ID NO:39, or SEQ ID NO:40, or a fragment or variant thereof that exhibits antiviral activity. Methods of the invention can also further comprise administering one or more compounds useful for treating a viral infection or viral associated disorder. Such compounds can be administered prior to, in conjunction with, and/or subsequent to administration of a peptide, polynucleotide, and/or composition of the present invention. The patient can be a human or other mammal, such as a dog, cat, or horse, or other animals having the disorder. Means for administering and formulating peptides and polynucleotides for administration to a patient are known in the art, examples of which are described herein. Peptides, polynucleotides, and/or compositions of the invention can be delivered to a cell either through direct contact of peptide, polynucleotide, or composition with the cell or via a carrier means. In one embodiment, a peptide, polynucleotide, or composition of the invention comprises an attached group that enhances cellular uptake of the peptide. In one embodiment, the peptide, polynucleotide, or composition is attached to an antibody that binds to a targeted cell. In another embodiment, the peptide, polynucleotide, or composition is encapsulated in a liposome. Peptides can also be delivered using a polynucleotide that encodes a subject peptide. Any polynucleotide having a nucleotide sequence that encodes a peptide of the invention is contemplated within the scope of the invention. In one embodiment, the polynucleotide is delivered to the cell where it is taken up and the polynucleotide is transcribed into RNA and the RNA is translated into the encoded peptide. Examples of viruses whose replication can be inhibited using the present invention include, but are not limited to, herpes viruses, poxviruses, and picornaviruses, such as vaccinia virus, EMC virus, influenza virus, herpes zoster virus, cytomegalovirus, and herpes simplex virus (e.g., HSV-1).

For the treatment of viral infections, the peptides, polynucleotides, and compositions of this invention can be administered to a patient in need of treatment in combination with other antiviral substances. These other antiviral substances may be given at the same or different times as the peptides, polynucleotides, and compositions of this invention. For example, the peptides, polynucleotides, and compositions of the present invention can be used in combination with one or more viral inhibitors such as interferons, and/or other drugs or antibodies, such as IFN$\alpha$, IFN$\beta$, IFN$\gamma$, acyclovir (ZOVIRAX), zidovudine (ZDV) (RETROVIR), lamivudine (3TC) (EPIVIR), zanamivir (RELENZA), oseltamivir (TAMIFLU), valacyclovir (VALTREX), amantadine (SYMMETREL), rimantadine (FLUMADINE), cidofovir (VISTIDE), foscarnet (FOSCAVIR), ganciclovir (CYTOVENE), ribavirin (VIRAZOLE), nelfinavir (VIRACEPT), ritonavir (NORVIR), rifampin (RIFADIN), and famciclovir (FAMVIR).

The subject invention also concerns methods for treating an oncological disorder or an autoimmune disorder in a patient. In one embodiment, an effective amount of a peptide, polynucleotide, or composition of the present invention that is an agonist of a type I IFN protein is administered to a patient having an oncological disorder or an autoimmune disorder and who is in need of treatment thereof. The subject invention also concerns methods for inhibiting the growth of a cancer cell by contacting the cell in vitro or in vivo with an effective amount of a peptide, polynucleotide, or composition of the present invention. The subject invention also concerns methods for activating an immune cell (e.g., T cell, NK cell, macrophage, etc.), and/or upregulating antigen presentation to lymphocytes, and/or upregulating major histocompatibility complex (MHC) molecules, and/or activating a JAK/STAT pathway, and/or activating TYK2 in a cell by contacting the cell in vitro or in vivo with an effective amount of a peptide, polynucleotide, or composition of the present invention. In one embodiment, the peptide has the amino acid sequence in SEQ ID NO:1, SEQ ID NO:2, SEQ ID NO:3, SEQ ID NO:4, SEQ ID NO:5, SEQ ID NO:6, SEQ ID NO:38, SEQ ID NO:39, or SEQ ID NO:40, or a fragment or variant thereof that exhibits anticancer activity. Methods of the invention can also further comprise administering or contacting a cell with one or more compounds for treating an oncological or autoimmune disorder. Such compounds can be administered prior to, in conjunction with, and/or subsequent to administration of a peptide, polynucleotide, and/or composition of the present invention. Methods of the invention can optionally include identifying a patient who is or may be in need of treatment of an oncological or autoimmune disorder. The patient can be a human or other mammal, such as a primate (monkey, chimpanzee, ape, etc.), dog, cat, cow, pig, or horse, or other animals having an oncological disorder. Means for administering and formulating peptides, polynucleotides, or compositions of the invention for administration to a patient are known in the art, examples of which are described herein. Autoimmune disorders within the scope of the invention include, but are not limited to, multiple sclerosis and rheumatoid arthritis. In one embodiment, a huIFN$\beta$1(100-187) (SEQ ID NO:2) peptide or huIFN$\beta$1(150-187) (SEQ ID NO:39) peptide, or a polynucleotide encoding the peptide, is used to treat a person or animal having multiple sclerosis. Oncological disorders within the scope of the invention include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment with the present invention include carcinomas, Kaposi's sarcoma, melanoma, mesothelioma, soft tissue sarcoma, pancreatic cancer, lung cancer, leukemia (hairy cell, acute lymphoblastic, acute myeloid, chronic lymphocytic, chronic myeloid, and other), and lymphoma (Hodgkin's and non-Hodgkin's), and follicular lymphoma, and multiple myeloma. In one embodiment, a huIFN$\alpha$2 (SEQ ID NO:5) peptide, or a polynucleotide encoding the peptide, is used to treat a person or animal having a melanoma.

Examples of cancers that can be treated according to the present invention are listed in Table 3.

TABLE 3

| Examples of Cancer Types | |
|---|---|
| Acute Lymphoblastic Leukemia, Adult | Hairy Cell Leukemia |
| Acute Lymphoblastic Leukemia, Childhood | Head and Neck Cancer |
| Acute Myeloid Leukemia, Adult | Hepatocellular (Liver) Cancer, Adult (Primary) |
| Acute Myeloid Leukemia, Childhood | Hepatocellular (Liver) Cancer, Childhood |

TABLE 3-continued

| Examples of Cancer Types | |
|---|---|
| Adrenocortical Carcinoma | (Primary) |
| Adrenocortical Carcinoma, Childhood | Hodgkin's Lymphoma, Adult |
| AIDS-Related Cancers | Hodgkin's Lymphoma, Childhood |
| AIDS-Related Lymphoma | Hodgkin's Lymphoma During Pregnancy |
| Anal Cancer | Hypopharyngeal Cancer |
| Astrocytoma, Childhood Cerebellar | Hypothalamic and Visual Pathway Glioma, |
| Astrocytoma, Childhood Cerebral | Childhood |
| Basal Cell Carcinoma | Intraocular Melanoma |
| Bile Duct Cancer, Extrahepatic | Islet Cell Carcinoma (Endocrine Pancreas) |
| Bladder Cancer | Kaposi's Sarcoma |
| Bladder Cancer, Childhood | Kidney (Renal Cell) Cancer |
| Bone Cancer, Osteosarcoma/Malignant | Kidney Cancer, Childhood |
| Fibrous Histiocytoma | Laryngeal Cancer |
| Brain Stem Glioma, Childhood | Laryngeal Cancer, Childhood |
| Brain Tumor, Adult | Leukemia, Acute Lymphoblastic, Adult |
| Brain Tumor, Brain Stem Glioma, | Leukemia, Acute Lymphoblastic, Childhood |
| Childhood | Leukemia, Acute Myeloid, Adult |
| Brain Tumor, Cerebellar Astrocytoma, | Leukemia, Acute Myeloid, Childhood |
| Childhood | Leukemia, Chronic Lymphocytic |
| Brain Tumor, Cerebral | Leukemia, Chronic Myelogenous |
| Astrocytoma/Malignant Glioma, | Leukemia, Hairy Cell |
| Childhood | Lip and Oral Cavity Cancer |
| Brain Tumor, Ependymoma, Childhood | Liver Cancer, Adult (Primary) |
| Brain Tumor, Medulloblastoma, | Liver Cancer, Childhood (Primary) |
| Childhood | Lung Cancer, Non-Small Cell |
| Brain Tumor, Supratentorial Primitive | Lung Cancer, Small Cell |
| Neuroectodermal Tumors, Childhood | Lymphoma, AIDS-Related |
| Brain Tumor, Visual Pathway and | Lymphoma, Burkitt's |
| Hypothalamic Glioma, Childhood | Lymphoma, Cutaneous T-Cell, see Mycosis |
| Brain Tumor, Childhood | Fungoides and Sézary Syndrome |
| Breast Cancer | Lymphoma, Hodgkin's, Adult |
| Breast Cancer, Childhood | Lymphoma, Hodgkin's, Childhood |
| Breast Cancer, Male | Lymphoma, Hodgkin's During Pregnancy |
| Bronchial Adenomas/Carcinoids, | Lymphoma, Non-Hodgkin's, Adult |
| Childhood | Lymphoma, Non-Hodgkin's, Childhood |
| Burkitt's Lymphoma | Lymphoma, Non-Hodgkin's During |
| Carcinoid Tumor, Childhood | Pregnancy |
| Carcinoid Tumor, Gastrointestinal | Lymphoma, Primary Central Nervous System |
| Carcinoma of Unknown Primary | Macroglobulinemia, Waldenström's |
| Central Nervous System Lymphoma, | Malignant Fibrous Histiocytoma of |
| Primary | Bone/Osteosarcoma |
| Cerebellar Astrocytoma, Childhood | Medulloblastoma, Childhood |
| Cerebral Astrocytoma/Malignant | Melanoma |
| Glioma, Childhood | Melanoma, Intraocular (Eye) |
| Cervical Cancer | Merkel Cell Carcinoma |
| Childhood Cancers | Mesothelioma, Adult Malignant |
| Chronic Lymphocytic Leukemia | Mesothelioma, Childhood |
| Chronic Myelogenous Leukemia | Metastatic Squamous Neck Cancer with |
| Chronic Myeloproliferative Disorders | Occult Primary |
| Colon Cancer | Multiple Endocrine Neoplasia Syndrome, |
| Colorectal Cancer, Childhood | Childhood |
| Cutaneous T-Cell Lymphoma, see | Multiple Myeloma/Plasma Cell Neoplasm |
| Mycosis Fungoides and Sézary | Mycosis Fungoides |
| Syndrome | Myelodysplastic Syndromes |
| Endometrial Cancer | Myelodysplastic/Myeloproliferative Diseases |
| Ependymoma, Childhood | Myelogenous Leukemia, Chronic |
| Esophageal Cancer | Myeloid Leukemia, Adult Acute |
| Esophageal Cancer, Childhood | Myeloid Leukemia, Childhood Acute |
| Ewing's Family of Tumors | Myeloma, Multiple |
| Extracranial Germ Cell Tumor, | Myeloproliferative Disorders, Chronic |
| Childhood | Nasal Cavity and Paranasal Sinus Cancer |
| Extragonadal Germ Cell Tumor | Nasopharyngeal Cancer |
| Extrahepatic Bile Duct Cancer | Nasopharyngeal Cancer, Childhood |
| Eye Cancer, Intraocular Melanoma | Neuroblastoma |
| Eye Cancer, Retinoblastoma | Non-Hodgkin's Lymphoma, Adult |
| Gallbladder Cancer | Non-Hodgkin's Lymphoma, Childhood |
| Gastric (Stomach) Cancer | Non-Hodgkin's Lymphoma During Pregnancy |
| Gastric (Stomach) Cancer, Childhood | Non-Small Cell Lung Cancer |
| Gastrointestinal Carcinoid Tumor | Oral Cancer, Childhood |
| Germ Cell Tumor, Extracranial, | Oral Cavity Cancer, Lip and |
| Childhood | Oropharyngeal Cancer |
| Germ Cell Tumor, Extragonadal | Osteosarcoma/Malignant Fibrous |
| Germ Cell Tumor, Ovarian | Histiocytoma of Bone |
| Gestational Trophoblastic Tumor | Ovarian Cancer, Childhood |
| Glioma, Adult | Ovarian Epithelial Cancer |
| Glioma, Childhood Brain Stem | Ovarian Germ Cell Tumor |
| Glioma, Childhood Cerebral | Ovarian Low Malignant Potential Tumor |
| Astrocytoma | Pancreatic Cancer |

TABLE 3-continued

| Examples of Cancer Types | |
|---|---|
| Glioma, Childhood Visual Pathway and Hypothalamic | Pancreatic Cancer, Childhood |
| Skin Cancer (Melanoma) | Pancreatic Cancer, Islet Cell |
| Skin Carcinoma, Merkel Cell | Paranasal Sinus and Nasal Cavity Cancer |
| Small Cell Lung Cancer | Parathyroid Cancer |
| Small Intestine Cancer | Penile Cancer |
| Soft Tissue Sarcoma, Adult | Pheochromocytoma |
| Soft Tissue Sarcoma, Childhood | Pineoblastoma and Supratentorial Primitive Neuroectodermal Tumors, Childhood |
| Squamous Cell Carcinoma, see Skin Cancer (non-Melanoma) | Pituitary Tumor |
| Squamous Neck Cancer with Occult Primary, Metastatic | Plasma Cell Neoplasm/Multiple Myeloma |
| Stomach (Gastric) Cancer | Pleuropulmonary Blastoma |
| Stomach (Gastric) Cancer, Childhood | Pregnancy and Breast Cancer |
| Supratentorial Primitive Neuroectodermal Tumors, Childhood | Pregnancy and Hodgkin's Lymphoma |
| T-Cell Lymphoma, Cutaneous, see Mycosis Fungoides and Sézary Syndrome | Pregnancy and Non-Hodgkin's Lymphoma |
| Testicular Cancer | Primary Central Nervous System Lymphoma |
| Thymoma, Childhood | Prostate Cancer |
| Thymoma and Thymic Carcinoma | Rectal Cancer |
| Thyroid Cancer | Renal Cell (Kidney) Cancer |
| Thyroid Cancer, Childhood | Renal Cell (Kidney) Cancer, Childhood |
| Transitional Cell Cancer of the Renal Pelvis and Ureter | Renal Pelvis and Ureter, Transitional Cell Cancer |
| Trophoblastic Tumor, Gestational | Retinoblastoma |
| Unknown Primary Site, Carcinoma of, Adult | Rhabdomyosarcoma, Childhood |
| Unknown Primary Site, Cancer of, Childhood | Salivary Gland Cancer |
| Unusual Cancers of Childhood | Salivary Gland Cancer, Childhood |
| Ureter and Renal Pelvis, Transitional Cell Cancer | Sarcoma, Ewing's Family of Tumors |
| Urethral Cancer | Sarcoma, Kaposi's |
| Uterine Cancer, Endometrial | Sarcoma, Soft Tissue, Adult |
| Uterine Sarcoma | Sarcoma, Soft Tissue, Childhood |
| Vaginal Cancer | Sarcoma, Uterine |
| Visual Pathway and Hypothalamic Glioma, Childhood | Sezary Syndrome |
| Vulvar Cancer | Skin Cancer (non-Melanoma) |
| Waldenström's Macroglobulinemia | Skin Cancer, Childhood |
| Wilms' Tumor | |

For the treatment of oncological disorders, the peptides, polynucleotides, and compositions of this invention can be administered to a patient in need of treatment in combination with other antitumor or anticancer substances and/or with radiation and/or photodynamic therapy and/or with surgical treatment to remove a tumor. These other substances or treatments may be given at the same as or at different times from the peptides, polynucleotides, and compositions of this invention. For example, the peptides, polynucleotides, and compositions of the present invention can be used in combination with mitotic inhibitors such as taxol or vinblastine, alkylating agents such as cyclophosphamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. Peptides, polynucleotides, and compositions of the invention can be used in combination with proteasome inhibitors, including, but not limited to, Bortezomib (VELCADE), Carfilzomib (KYPROLIS), and Salinosporamide A. The subject invention also concerns methods for inhibiting the growth of a cancer cell by contacting the cell in vitro or in vivo with an effective amount of a peptide, polynucleotide, or composition of the present invention.

Many tumors and cancers have viral genome present in the tumor or cancer cells. For example, Epstein-Barr Virus (EBV) is associated with a number of mammalian malignancies. The peptides, polynucleotides, and compositions of the subject invention can also be used alone or in combination with anticancer or antiviral agents, such as ganciclovir (CYTOVENE), azidothymidine (AZT) (RETROVIR), lamivudine (3TC) (EPIVIR), etc., to treat patients infected with a virus that can cause cellular transformation and/or to treat patients having a tumor or cancer that is associated with the presence of viral genome in the cells.

The methods of the present invention can be used with humans and other animals. The other animals contemplated within the scope of the invention include domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses.

In one embodiment, one or more of the peptides of the subject invention can be provided in the form of a multiple peptide construct. Such a construct can be designed so that multiple peptides are linked to each other by intervening moieties wherein the intervening moieties are subsequently cleaved or removed following administration of the multiple peptide construct to a patient. Methods for constructing multiple peptide constructs are known in the art. For example, peptides of the present invention can be provided in the form of a multiple antigenic peptide (MAP) construct. The preparation of MAP constructs has been described in Tam (1988). MAP constructs utilize a core matrix of lysine residues onto which multiple copies of an immunogen are synthesized. Multiple MAP constructs, each containing different peptides, can be prepared and administered in accordance with methods of the present invention. In another embodiment, a multiple peptide construct can be prepared by preparing the subject peptides having at least one metal chelating amino acid incorporated therein, preferably at the amino and/or carboxy terminal of the peptide as described, for example, in U.S. Pat. No. 5,763,585. The peptides are then contacted with a solid support having attached thereto a metal ion specific for the metal chelating amino acid of the peptide. A multiple peptide construct of the invention can provide multiple copies of the exact same peptide, including variants or fragments of a subject peptide, or copies of different peptides of the subject invention.

Therapeutic application of the subject peptides, polynucleotides, and compositions containing them, can be accomplished by any suitable therapeutic method and technique presently or prospectively known to those skilled in the art. The peptides and polynucleotides can be administered by any suitable route known in the art including, for example, oral, nasal, rectal, parenteral, subcutaneous, or intravenous routes of administration. Administration of the peptides and polynucleotides of the invention can be continuous or at distinct intervals as can be readily determined by a person skilled in the art.

Compounds and compositions useful in the subject invention can be formulated according to known methods for preparing pharmaceutically useful compositions. Formulations are described in detail in a number of sources which are well known and readily available to those skilled in the art. For example, *Remington's Pharmaceutical Science* by E.W. Martin describes formulations which can be used in connection with the subject invention. In general, the compositions of the subject invention will be formulated such that an effective amount of the bioactive peptide or polynucleotide is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject peptides and polynucleotides include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of the peptide or polynucleotide of the invention can also comprise suspension agents, protectants, lubricants, buffers, preservatives, and stabilizers. To provide for the administration of such dosages for the desired therapeutic treatment, pharmaceutical compositions of the invention will advantageously comprise between about 0.1% and 45%, and especially, 1 and 15% by weight of the total of one or more of the peptide or polynucleotide based on the weight of the total composition including carrier or diluent.

The peptides, polynucleotides, and compositions of the subject invention can also be administered utilizing liposome technology, slow release capsules, implantable pumps, and biodegradable containers. These delivery methods can, advantageously, provide a uniform dosage over an extended period of time.

The subject peptides and polynucleotides can also be modified by the addition of chemical groups, such as PEG (polyethylene glycol). PEGylated peptides typically generate less of an immunogenic response and exhibit extended half-lives in vivo in comparison to peptides that are not PEGylated when administered in vivo. Methods for PEGylating proteins and peptides known in the art (see, for example, U.S. Pat. No. 4,179,337). The subject peptides and polynucleotides can also be modified to improve cell membrane permeability. In one embodiment, cell membrane permeability can be improved by attaching a lipophilic moiety, such as a steroid, to the peptide or polynucleotide. In another embodiment, peptides and polynucleotides of the invention comprise a cell-penetrating peptide (CPP). CPPs are typically short peptides that are highly cationic and typically include several arginine and/or lysine amino acids. CPPs can be classified as hydrophilic, amphiphilic, or periodic sequence. In one embodiment, a CPP is provided at the terminus of a peptide or polynucleotide. Examples of CPPs include, but are not limited to penetratin or antenapedia PTD (RQIKWFQNRRMKWKK) (SEQ ID NO:19), TAT (YGRKKRRQRRR) (SEQ ID NO:20), SynB1 (RGGRLSYSRRRFSTSTGR) (SEQ ID NO:21), SynB3 (RRLSYSRRRF) (SEQ ID NO:22), PTD-4 (PIRRRKKLRRLK) (SEQ ID NO:23), PTD-5 (RRQRRTSKLMKR) (SEQ ID NO:24), FHV Coat-(35-49) (RRRRNRTRRNRRRVR) (SEQ ID NO:25), BMV Gag-(7-25) (KMTRAQRRAAARRNRWTAR) (SEQ ID NO:26), HTLV-II Rex-(4-16) (TRRQRTRRARRNR) (SEQ ID NO:27), D-Tat (GRKKRRQRRRPPQ) (SEQ ID NO:28), R9-Tat (GRRRRRRRRRPPQ) (SEQ ID NO:29), Transportan (GWTLNSAGYLLGKINLKALAALAKKIL) (SEQ ID NO:30) chimera, MAP (KLALKLALKLALALKLA) (SEQ ID NO:31), SBP (MGLGLHLLVLAAALQGAWSQPKKKRKV) (SEQ ID NO:32), FBP (GALFLGWLGAAGSTMGAWSQPKKKRKV) (SEQ ID NO:33), MPG (ac-GALFLGFLGAAGSTMGAWSQPKKKRKV-cya) (SEQ ID NO:34), MPG$^{(\Delta NLS)}$ (ac-GALFLGFLGAAGSTMGAWSQPKSKRKV-cya) (SEQ ID NO:35), Pep-1 (ac-KETWWETWWTEWSQPKKKRKV-cya) (SEQ ID NO:36), and Pep-2 (ac-KETWFETWFTEWSQPKKKRKV-cya) (SEQ ID NO:37). Other CPPs can have only arginine (R) or only lysine (K) amino acids, e.g., having a formula $(R)_n$ or $(K)_n$, where n=an integer from 3 to 20 (e.g., SEQ ID NO:43). Other groups known in the art for providing for cell membrane permeability can be linked to peptides and polynucleotides of the present invention.

The subject invention also concerns a packaged dosage formulation comprising in one or more containers at least one peptide, polynucleotide, and/or composition of the subject invention formulated in a pharmaceutically acceptable dosage. The package can contain discrete quantities of the dosage formulation, such as tablet, capsules, lozenge, and powders. The quantity of peptide and/or polynucleotide in a dosage formulation and that can be administered to a patient can vary from about 1 mg to about 5000 mg, or about 1 mg to about 2000 mg, or more typically about 1 mg to about 500 mg, or about 5 mg to about 250 mg, or about 10 mg to about 100 mg.

The subject invention also concerns kits comprising one or more peptides, polynucleotides, compositions, compounds, or molecules of the present invention in one or more containers. In one embodiment, a kit contains a peptide, polynucleotide, and/or composition of the present invention. In a specific embodiment, a kit comprises a peptide comprising the amino acid sequence shown in SEQ ID NO:1, SEQ ID NO:2, SEQ ID NO:3, SEQ ID NO:4, SEQ ID NO:5, SEQ ID NO:6, SEQ ID NO:38, SEQ ID NO:39, or SEQ ID NO:40, or a fragment or variant of the peptide that exhibits substantially the same activity as the full-length non-variant peptide. A kit of the invention can also comprise one or more antiviral compounds, biological molecules, or drugs and/or one or more type I IFN peptide mimetics. In one embodiment, the biological molecule is one or more of IFNα, IFNβ, or IFNγ. In one embodiment, in addition to a peptide, polynucleotide, composition, or compound of the invention, a kit also comprises one or more peptides of SEQ ID NO:7 (MuIFNγ(95-132)) and/or SEQ ID NO:8 (huIFNγ(95-134)), and/or SEQ ID NO:9 (Tkip peptide), and/or SEQ ID NO:10, or a fragment or variant thereof that exhibits antiviral activity. In one embodiment, a kit comprises one or more of IFNα, IFNβ, IFNγ, acyclovir (ZOVIRAX), zidovudine (ZDV) (RETROVIR), lamivudine (3TC) (EPIVIR), zanamivir (RELENZA), oseltamivir (TAMIFLU), valacyclovir (VALTREX), amantadine (SYMMETREL), rimantadine (FLUMADINE), cidofovir (VISTIDE), foscarnet (FOSCAVIR), ganciclovir (CYTOVENE), ribavirin (VIRAZOLE), nelfinavir (VIRACEPT), ritonavir (NORVIR), rifampin (RIFADIN), and famciclovir (FAMVIR). In another embodiment, a kit comprises one or more of mitotic inhibitors such as taxol or vinblastine, alkylating agents such as cyclophosphamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

In one embodiment, a kit of the invention includes instructions or packaging materials that describe how to administer a peptide, polynucleotide, compositions, compounds, or molecules of the kit. Containers of the kit can be of any suitable material, e.g., glass, plastic, metal, etc., and of any suitable size, shape, or configuration. In one embodiment, a peptide, polynucleotide, compositions, compounds, or molecules of the invention is provided in the kit as a solid, such as a tablet, pill, or powder form. In another embodiment, a peptide, polynucleotide, compositions, compounds, or molecules of the invention is provided in the kit as a liquid or solution. In one embodiment, the kit comprises an ampoule or syringe containing a peptide, polynucleotide, compositions, compounds, or molecules of the invention in liquid or solution form.

The subject invention also concerns methods for inhibiting type I IFN cell activation and/or intracellular signaling. In one embodiment, an inhibitor of an IFNAR is provided in a cell. In a further embodiment, the IFNAR is IFNAR1 or IFNAR2. The cell can be a mammalian cell, such as a human cell. In one embodiment, the cell is infected with a virus. Any suitable inhibitor that can inhibit the function of an IFNAR is contemplated within the scope of the invention. Examples of inhibitors include, but are not limited to, antibodies (and antigen binding fragments thereof) and other compounds or agents that bind to an IFNAR.

Materials and Methods for Examples 1-6

Cell Culture and Abs

WISH and Daudi cells were purchased from American Type Culture Collection (ATCC) and were grown in MEME and RPMI (Sigma-Aldrich), respectively, with 10% FBS and antibiotics. For all experiments, cells were serum starved for at least 4 hours, washed twice with PBS and then given serum free media with or without 1,000 U/ml IFNα2 (Calbiochem) or IFN. The following polyclonal antisera were purchased from Santa Cruz Biotech: IFNAR1, IFNAR2, STAT1, pSTAT1, STAT2, pSTAT2, TYK2, pTYK2, normal rabbit IgG, β-Tubulin, β-Lamin, and Histone H3. The following polyclonal antisera were purchased from Active Motif: H3K9ac and H3K9me3. Additional Abs to TYK2 and IFNAR1 were also purchased from BD Bioscience and Epitomics, respectively. We produced the antibody to tyrosine phosphorylated histone H3 by immunization of rabbits with histone H3 peptide, $^{33}$GGVKKPHRpYRPGTVAL-REIR (SEQ ID NO:13), with a phosphate at tyrosine 41. We tested antibodies to some proteins from different sources to monitor the specificity.

Chromatin Immunoprecipitation (ChIP) Assay

WISH cells were treated or not with type I IFN for 1 hr. Cells were then washed twice with cold PBS and treated with 1% formaldehyde for 10 min at 37° C. The rest of the procedure was conducted using the ChIP kit from Millipore, as per the manufacturer's protocol. Sonication was conducted to get DNA fragments of ~500 bp. Control IgG, or different Abs, were used for each immunoprecipitation as indicated. DNA fragments eluted were used for PCR with the following primers that spanned the ISRE element in their promoters. Human OAS1 promoter region was amplified with the primers 5'-CATTGACAGGAGAGAGAGTG-3' (SEQ ID NO:14) (−147 to −133) and 5'-TCAGGGGAGT-GTCTGATTTG-3' (SEQ ID NO:15) (−17 to +3). As a control, PCR was conducted with the primers from the human β-actin promoter 5'-CTCGCTCTCGCTCTTTTTTTTTTTC-3' (SEQ ID NO:16) (−967 to −941) and 5'-CTCGAGC-CATAAAAGGCAACT-3' (SEQ ID NO:17) (−844 to −864). The PCR conditions were as follows: heating at 94° C. for 5 min, followed by 35 cycles at 94° C. for 15 sec, 60° C. for 30 sec, and 68° C. for 15 sec. This was followed by annealing at 68° C. for 5 min. Following ChIP with the indicated Abs, the DNA protein complex was used to elute the associated proteins by boiling with the electrophoresis buffer and was analyzed by Western blotting as mentioned before (Noon-Song et al., 2011).

Isolation of Nuclei

IFN treated WISH cells were washed twice in cold PBS, removed by scraping in lysis buffer (10 mM HEPES pH 7.9, 100 mM KCl, 1% Triton X-100, 1 mM NaF, 1 mM Na$_3$VO$_4$, 2 mM MgCl$_2$, 1 mM DTT, and 1 mM PMSF), and pelleted by low speed centrifugation. The supernatant was saved as cytoplasmic fraction. The pellet containing intact nuclei, was gently resuspended in lysis buffer. The centrifugation, re-suspension, and decanting was then repeated twice more. Isolated nuclei were confirmed by trypan blue staining.

Western Blot Analysis and Immunoprecipitation Cells were washed with PBS and harvested in lysis buffer (10 mM HEPES pH 7.9, 100 mM KCl, 1% Triton X-100, 1 mM NaF, 1 mM Na$_3$VO$_4$, 2 mM MgCl$_2$, 1 mM DTT, and 1 mM PMSF). Whole cell lysate was generated via sonication on ice and insoluble material removed via centrifugation at 14 k rpm for 10 min at 4° C. Protein concentration was measured using 660 nm protein assay reagent (Pierce). Protein (10 μg each) was electrophoresed on an acrylamide gel, transferred to PVDF membrane, and probed with the indicated Abs. HRP-conjugated secondary Abs were then added and detection was conducted by chemiluminescence (Pierce). Immunoprecipitation was conducted by incubating specific Abs with equal amounts of lysate, followed by incubation with Protein A-Agarose (Santa Cruz Biotech) for at least 2 hours. Precipitated material was sedimented and washed thrice with PBS. Pellets were taken in electrophoresis buffer, boiled and loaded on an acrylamide gel, transferred and probed with antibodies indicated.

Expression and Purification of Type I IFN Mimetics

Type I IFN mimetics were expressed as follows. The coding sequence for human IFNα1, IFNα1 (69-189), preceded by nine arginine (R9) residues (for cell penetration) was inserted in the bacterial expression vector, pET30a+. The coding sequence for human IFNβ, IFNβ(100-187) preceded by R9 was similarly inserted into pET30a+. As controls, the human IFNα1(69-189) or IFNβ(100-187) without the R9 were also inserted in pET30a+. *E. coli* BL21 (DE3) Rosetta strain was used to transform the expression sequence in pET30a+. After the bacterial growth had reached the mid-log phase, induction with 0.5 mM IPTG was carried out and growth continued for 4 hours. The proteins were purified by using the Ni-NTA His Bind Resin (Novagen). The His tag was removed by digesting with enterokinase. The purity of the protein was assessed by SDS-PAGE analysis and coomassie blue staining.

GFP Fusion Constructs and Microscopy

The coding sequence from IFNτ, IFNAR1, or IFNAR2 was used to generate a PCR product that was fused in frame with the C terminus of humanized rGFP in the plasmid phrGFPII-C (Stratagene). WISH cells that were grown on coverslips to near 30% confluency in a 35 mm dish were transfected using lipofectamine (Invitrogen Life Technologies), with 3 μg of the empty vector or the IFNτ fused GFP vector. IFNAR1 or IFNAR2 sequences fused to GFP were similarly transfected. Where indicated, IFNτ was added at 1,000 U/ml. Next day, cells were fixed with 2% paraformaldehyde in PBS, mounted on a slide, and viewed in a Zeiss Axiovert Zoom confocal microscope using LSM Pascal software, as described before (Ahmed and Johnson, 2006).

Antiviral Assay

Antiviral assays were performed by using a cytopathic effect (CPE) reduction assay using encephalomyocarditis (EMC) virus. WISH cells (40,000 per well in a microtiter dish) were grown overnight. IFNα1(69-189)R9, IFNβ(100-187)R9, or their controls without the R9 sequence were added to cells at the concentrations indicated for 4 hr, followed by infection with EMCV (moi=0.01). Virus was washed after one hr and cells were grown overnight. Cells were stained with crystal violet and read in a microtiter plate at 550 nm.

Induction of EAE, Evaluation of Clinical Disease, and Administration of Peptides Female SJL/J mice (6 to 8 weeks old) were purchased from Jackson Laboratories (Bar Harbor, Me.) and housed in standard SPF facilities. On day 1, SJL/J mice were injected with 300 μg/mouse bovine myelin basic protein (Invitrogen) emulsified in Complete Freund's Adjuvant with 8 mg/ml H37Ra *Mycobacterium tuberculosis* (Sigma-Aldrich) and injected subcutaneously into two sites at the base of the tail along with 400 ng/mouse pertussis toxin (List Biological Laboratories Inc) in PBS i.p. On day 3, the pertussis toxin injection was repeated (Jager et al., 2011). Beginning on day 12 post-immunization, after lymphocyte infiltration of the CNS had begun, mice were administered the following treatments or peptides every other day via i.p. injection in 100 μl final volume: PBS, IFNα1(69-189)R9 (15 μg/mouse), or IFNα1(69-189) (15 μg/mouse). The mice were monitored daily for signs of EAE and graded according to the following scale: 0, normal; 1, loss of tail tone; 2, hind limb weakness; 3, paraparesis; 4, paraplegia; 5, moribund; and 6, death. The Institutional Animal Care and Use Committee at the University of Florida approved all of the animal protocols mentioned here.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Activated TYK2, JAK1, and Interferon Alpha/Beta Receptor Subunits (IFNAR1 and IFNAR2) in the Nucleus of Type I IFN Treated Cells We have recently shown that treatment of WISH cells with IFNγ resulted in the presence of activated JAK1 and JAK2 in the nucleus (Noon-Song et al., 2011). We thus treated WISH cells with type I IFNs IFNα2 and IFNτ, which have similar specific antiviral activities, but IFNα2 with much more potent apoptosis activity (Subramaniam et al., 1995). The focus was on the presence of activated TYK2, JAK1, and receptor subunits IFNAR1 and IFNAR2 in the nucleus of cells treated with type I IFNs. At a concentration of 1000 U/ml, IFNα2 treatment resulted in the presence of both phosphorylated (activated) JAKs, pJAK1 and pTYK2, in the nucleus (FIG. 1A). Nonphosphorylated TYK2 was constitutively present in the nucleus of untreated cells. Nonphosphorylated JAK1 was also present in the nucleus (data not shown). IFNτ treatment similarly resulted in the presence of pTYK2 in the nucleus (FIG. 1B). Both phosphorylated STAT1β and STAT2 were detected in the nucleus only after treatment of cells with the IFNs (FIGS. 1A and 1B). To ascertain the purity of nuclear fractionations, β-tubulin and β-lamin were used as markers of nuclear and cytoplasmic fractions, respectively (FIGS. 1A, 1B, and 1C).

Focus on activated JAKs in the nucleus without context, although of some interest, provides little insight into their role in specific gene activation. Thus, we also examined the movement of type I IFN receptor subunit IFNAR1 into the nucleus of WISH cells treated with the IFNs. For both IFNα2 (FIG. 1A) and IFNτ (FIG. 1B), IFN treatment resulted in the presence of IFNAR1 in the nucleus. There were relatively low or trace amounts of IFNAR1 in the nucleus of untreated cells, which increased several fold after treatment with IFNα2 or IFNτ. This is consistent with a low constitutive endogenous level of IFNβ in untreated cells (Takoka et al., 2000; Taniguchi and Takaoka, 2008). This constitutive IFNβ has been shown to be important for priming cells for both induction of type I IFNs and in enhancement of the cellular response to both IFNγ and type I IFNs. We also determined that IFNAR2 similarly underwent nuclear translocation in IFNτ treated WISH cells (FIG. 1C). The movement of IFNAR1 and IFNAR2 into the nucleus along with the JAKs suggests an association of the two events. Consistent with these results, we have identified a functional nuclear localization sequence in IFNAR1 (Subramaniam and Johnson, 2004) and IFNAR2 ($^{283}$RKKK (SEQ ID NO:18); unpublished observation) and a putative NLS in TYK2 (Ragimbeau et al., 2001).

Figure 2A:
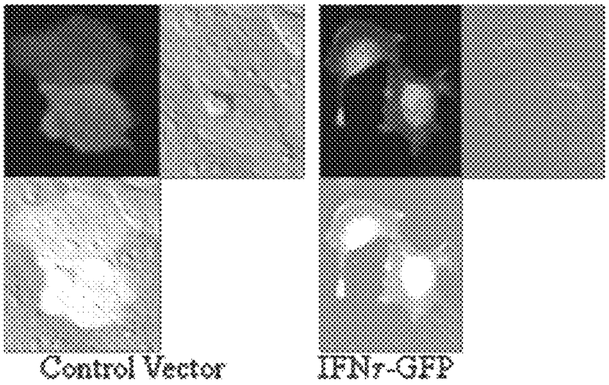
FIGS. 2A-2C. Nuclear translocation of IFNτ, IFNAR1, and IFNAR2 as determined by confocal microscopy. GFP fusion constructs of IFNτ, IFNAR1, and IFNAR2 were used to separately transfect WISH cells (see MATERIALS and METHODS). IFNτ-GFP transfected cells measured nuclear translocation of IFNτ (FIG. 2A). In the case of IFNAR1-GFP (FIG. 2B) and IFNAR2-GFP (FIG. 2C), cells were treated with 1,000 U/ml of IFNτ and receptors were found to translocate to nuclei as seen by confocal microscopy.
Figure 2B:
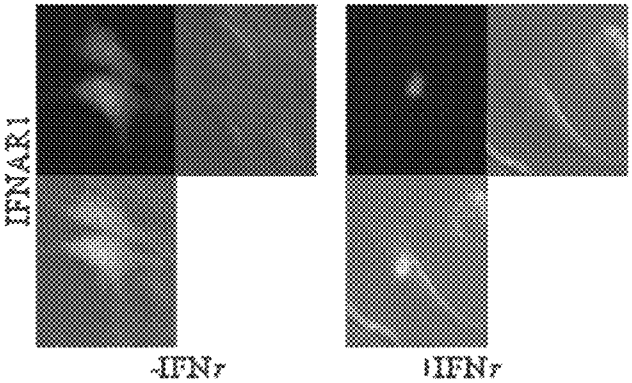
Figure 2C:
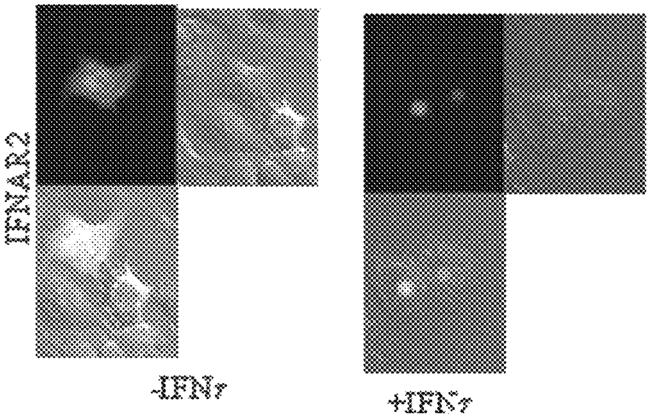

To further verify the movement of IFNAR1 and IFNAR2 into the nucleus of IFN treated cells as well as to determine if the type I IFN similarly underwent nuclear import, we carried out confocal microscopy with GFP fusion proteins. Specifically, WISH cells were transfected separately with CMV promoter driven constructs of IFNτ, IFNAR1, or IFNAR2 fused to GFP. As control, WISH cells were also transfected with vector containing only GFP. As shown in FIG. 2A, IFNτ-GFP treated cells showed an increased presence of IFNτ-GFP in the nucleus, while control GFP was present throughout the cell. In IFNAR1-GFP transfected cells, treatment with IFNτ caused nuclear translocation, while untreated cells showed no preference of IFNAR1-GFP for the nucleus as shown in FIG. 2B. IFNAR2-GFP was similarly driven into the nucleus of cells treated with IFNτ as shown in FIG. 2C. Thus, the type I IFN IFNτ and receptor subunits IFNAR1 and IFNAR2 all undergo increased nuclear translocation in cells treated with the IFN. Possible small amounts of IFNAR1 and IFNAR2 in the nucleus of untreated cells would probably be due to the constitutive endogenous IFNβ (Takoka et al., 2000; Taniguchi and Takaoka, 2008). These findings differ from the IFNγ system in that IFNGR1 translocated to the nucleus, while the IFNGR2 receptor subunit remained in the plasma membranes after IFNγ treatment of cells where it provided JAK2 to IFNGR1 (Szente et al., 1995). Thus, although similar in nuclear events, the type I and type II IFN systems differ in terms of receptor movement.

Example 2—Recruitment of IFNAR1, TYK2, and STAT1, Along with Phosphorylation of Histone H3Y41 (H3pY41) at the ISRE in the Promoter Region of the OAS1 Gene of Cells Treated with Type I IFN To determine if the type I IFN players of FIG. 1 were specifically recruited to the promoter region of a gene activated by IFNα2 in cells, we performed ChIP assays. WISH cells were treated with 1000 U/ml of IFNτ for 1 hour and analyzed by ChIP of sonicated chromatin of approximately 500-bp fragments of DNA, followed by PCR. Chromatin fragments were immunoprecipitated with antibodies to IFNAR1, histone H3 tyrosine 41 (H3pY41), TYK2, and STAT1, followed by PCR of the OAS1 promoter region extending from nucleotides −147 to 3. As a control, PCR product for the promoter of β-actin gene, −967 to −844, was chosen for ChIP analysis. IgG did not interact with the promoter containing complex as a control for non-specific binding. As shown in FIG. 3, IFNAR1, H3pY41, TYK2, and STAT1 were associated with the ISRE element of the OAS1 promoter in IFNα2 treated cells. The β-actin gene is not activated by type I IFNs and ChIP analysis showed that receptor subunit IFNAR1, H3pY41, JAKs, and STAT1 were not associated at its promoter after IFNτ treatment. Studies of IFN signaling have tended to focus extensively on STATs when examining the promoter region of genes activated by IFN as well as by other factors that signal via the JAK/STAT pathway (Levy and Darnell, 2002). The ChIP data here provide insight into the mechanism of specific gene activation as well as the associated H3pY41 epigenetic event of the type I IFN signaling and suggest that STAT is but one player in these complex events.

Example 3—TYK2 Associates with IFNAR1 in the Nucleus of Cells Treated with Type I IFN The demonstration of activated JAK2V617F and cytokine activated JAK2 in the nucleus of cells and their phosphorylation of H3Y41 (H3pY41) in the chromatin did not address the fact that epigenetic events such as this must involve some mechanism of specificity (Dawson et al., 2009). JAK2V617F, for example, is associated with specific myeloproliferative disorders and cytokine activation of wild type nuclear JAK2 is associated with the specific biological effect of the particular cytokine We showed in FIG. 3 above that TYK2 and H3pY41 were specifically associated with the OAS1 promoter in cells treated with a type I IFN. Since IFNAR1 is specific to type I IFN signaling and was present along with TYK2 at the OAS1 promoter, we asked the question as to whether TYK2 and IFNAR1 were associated in the nucleus of cells treated with a type I IFN, as this would suggest a basis of specificity. Accordingly, the human fibroblast cells were treated with 1000 U/ml of IFNα2 for 30 min, after which the cells were lysed and nuclear and cytosolic fractions were isolated. The nuclear and cytoplasmic fractions were IPed with antibody to IFNAR1 and Western blotted with antibodies to IFNAR1, TYK2, activated STAT1α (pSTAT1α), and H3pY41. As can be seen in FIG. 4, nuclear TYK2, pSTAT1α, and H3pY41 showed increased binding to IFNAR1 in IFNα2 treated cells. IgG treated control cells did not show similar association in whole cell extracts (data not shown). This is evidence that TYK2 as well as pSTAT1α do not function alone or independently of the cytokine system whose function they are associated with in the nucleus at the level of gene activation.

Example 4—Specific Epigenetic Changes at the OAS1 Promoter of Cells Treated with a Type I IFN We showed by ChIP analysis that IFNτ treatment of cells resulted in specific binding of IFNAR1, STAT1α, and TYK2 to the ISRE of the promoter of the OAS1 gene.

We examine here associated epigenetic changes by similar ChIP analysis at the OAS1 promoter. FIG. 5A shows decreased trimethylated lysine 9 on histone H3, H3K9me3, in the OAS1 promoter region of cells treated with 1000 U/ml of IFNτ over 40 minutes. Acetylation of H3K9, H3K9ac, occurred concomitantly over the same time span. Demethylation/acetylation of H3K9 is associated with gene activation (Berger, 2007; Mehta et al., 2011). Related to this, phosphorylation of H3 at Y41, H3pY41, increased as H3K9me3 decreased over the same time period. Phosphorylation of H3Y41 was confirmed by Western blot (FIG. 5B). By comparison, the constitutively activated β-actin gene, which is not affected by IFN, showed constitutive H3K9ac, no H3pY41, and no H3 K9me3. The presence of activated JAKs at the OAS1 region of type I IFN treated cells may be related to H3Y41 phosphorylation which in turn could play a role in the demethylation and acetylation of H3K9 at the promoter region of the gene. These observations suggest that the receptor/transcription factor/JAK complex of type I IFN treated cells plays a key role in specific gene activation, including the associated events of heterochromatin modification.

Figure 6A:
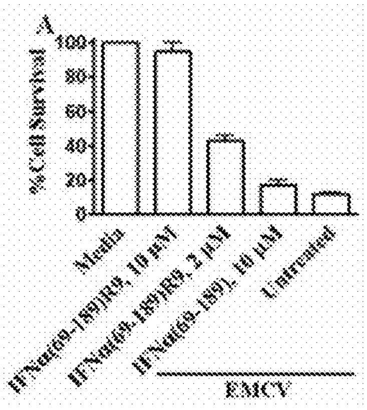
FIGS. 6A-6C. N-terminal truncated IFNα1(69-189)R9 or IFNβ(100-187)R9 possessed antiviral activity and IFNα1(69-189)R9 protected against relapsing/remitting EAE in SJL/J mice. IFNα1(69-189)R9 (FIG. 6A), or IFNβ(100-187)R9 (FIG. 6B), or the control peptides without the R9 plasma membrane penetration sequence were added to L929 cells (40,000 per well) and treated for 4 hr. Cells were infected with EMC virus (moi=0.01) for 24 hr, followed by staining with crystal violet.
Figure 6B:
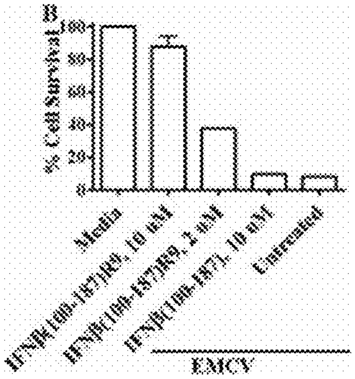

Example 5—N-Terminal Truncated Type I IFNs Lose Extracellular Activity while Retaining Intracellular Activity. Evidence of Cytoplasmic Binding In development of the IFNγ mimetics, we found that N-terminal truncations of IFNγ to IFNγ(95-132) for mouse and IFNγ(95-134) for human IFNγ resulted in loss of recognition of extracellular receptor (Szente et al., 1996; Ahmed et al., 2005). These truncated IFNs were, however, active when introduced intracellularly via a palmitate group with full antiviral activity (Ahmed et al., 2005). In order to determine if IFNα1 and IFNβ possessed similar C-terminus function intracellularly while losing extracellular function, we expressed truncated IFNα1(69-189)R9 and IFNβ (100-187)R9 with nine arginines (R9) for cell penetration in a bacterial expression system and purified the polypeptides. As controls, we also expressed these truncations without R9. Both IFNα1(69-189)R9 (FIG. 6A) and IFNβ(100-187)R9 (FIG. 6B) possessed antiviral activity against EMC virus, while the same constructs without R9 for cell penetration lacked antiviral activity. R9 alone also lacked antiviral activity (data not shown). This is consistent with previous studies that showed that intracellularly expressed IFNα possessed antiproliferative and antiviral activity (Ahmed et al., 2001). The truncation studies, however, are not subject to the argument that somehow the intracellular IFN may have leaked out of the cell and interacted with the extracellular receptor domains, since the truncations were not functional in terms of extracellular induced antiviral activity.

Figure 6C:
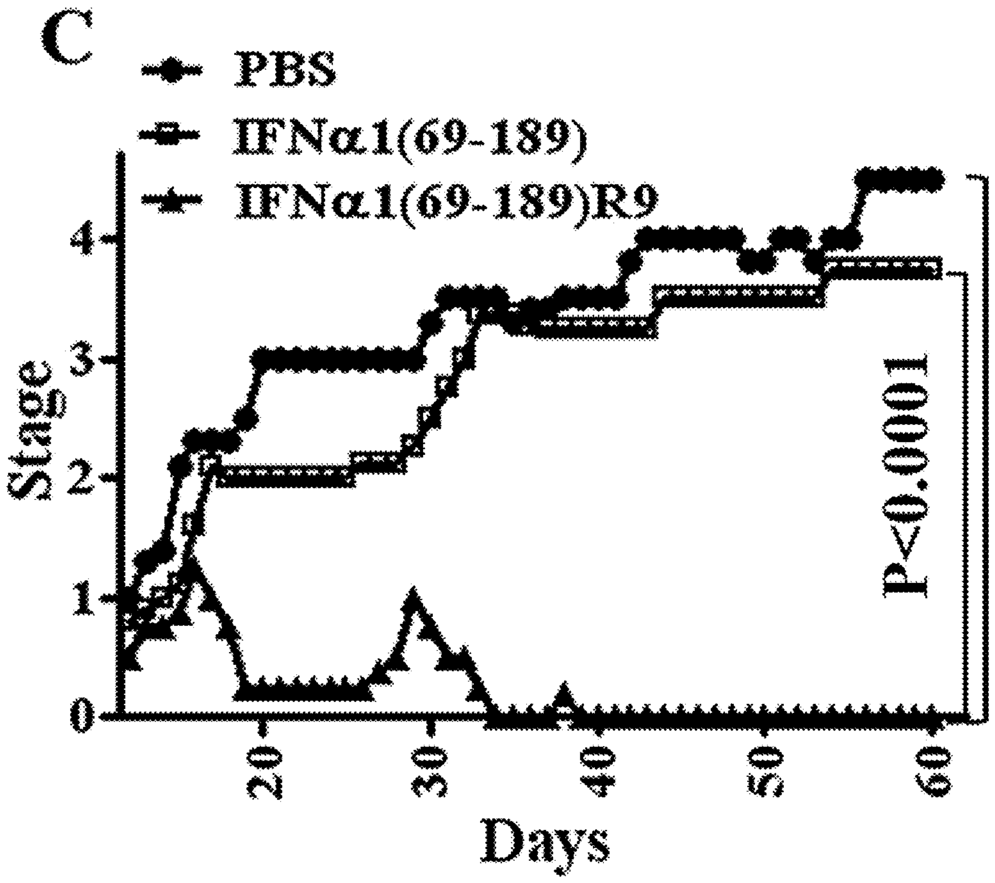

Type I IFN is the treatment of choice for relapsing/remitting multiple sclerosis (MS) (National Multiple Sclerosis Society Bulletin, 2012), so we tested IFNα1 (69-189) R9 for its ability to therapeutically treat SJL/J mice in experimental allergic encephalomyelitis (EAE), a mouse model of MS. Immunization of mice with bovine myelin basic protein (MBP) where cellular infiltration into the CNS has occurred by day 12 was used to test the truncated IFNs (Jager et al., 2011). IFNα(69-189)R9 administration beginning at day 12 and every other day thereafter remitted with essentially complete therapeutic efficacy, while IFNα1 (69-189) and PBS treated mice developed paraplegia (FIG. 6C).

The results presented here for induction of antiviral activity and EAE therapy by cell-penetrating truncated type I IFNs are inexplicable in the context of a model where the type I IFN exerts its effect solely by extracellular interaction with the receptor. The data are compatible with our IFNγ model where IFN after binding to receptor extracellular domain goes on to bind to the cytoplasmic domain of receptor in conjunction with endocytic events (Subramaniam and Johnson, 2002). The complex formation and the functional cytoplasmic activity of IFN truncations thus show similarities to steroid signaling (Johnson et al., 2012).

Example 6

Specific gene activation by cytokines such as the IFNs is attributed solely to the activated STATs (Levy and Darnell, 2002). In the case of IFNγ signaling, interaction of IFNγ with receptor results in autoactivation of JAK1 and JAK2, which in turn activate STAT1α in conjunction with receptor subunit IFNGR1. Activated STAT1α forms a homodimer, dissociates from IFNGR1, and undergoes active nuclear transport via an unconventional nuclear localization sequence (NLS) that associates with the importin α/β proteins (Johnson et al., 2004). The fact that STAT1α is activated by other cytokines in addition to IFNγ would suggest that STATs do not intrinsically contain the mechanism for specific gene activation by a particular cytokine (Johnson et al., 2012; Johnson et al., 2004; Johnson and Ahmed, 2006). This is reinforced by the fact that there are just seven STATs that function mostly as homodimeric transcription factors for over 60 different cytokines, growth factors, and hormones (Johnson et al., 2012; Johnson et al., 2004; Johnson and Ahmed, 2006).

Recently, nuclear JAK2 has been shown to play an important role at the epigenetic level in gene activation. Mutant activated JAK2, JAK2V617F, was shown to be constitutively present in the nucleus of effector cells of myeloproliferative disorders (Dawson et al., 2009). JAK2V617F was shown to phosphorylate tyrosine 41 on histone H3 (H3Y41), which is associated with gene activation. The constitutive activation of JAK2V617F required association with hematopoietic receptors such as that for erythropoietin (EPOR) at the cytoplasmic domain (Lu et al., 2008). The mechanism of how JAK2V617F underwent nuclear translocation as well as possible involvement of other proteins such as EPOR was not addressed. It was also shown that wild-type JAK2 was constitutively present in the nucleus of nonmyeloproliferative cell lines, but was only activated after treatment of K562 cells with PDGF or LIF or treatment of BaF3 cells with IL-3 (Dawson et al., 2009). As with JAK2V617F, the mechanism by which nonphosphorylated and phosphorylated JAK2 entered into the nucleus was not addressed.

Phosphorylation of H3Y41 by activated nuclear JAK2 assigns a previously unknown function to a JAK kinase. The presence of JAKs in the nucleus, phosphorylated and unphosphorylated, was however previously known. JAK1, JAK2, and TYK2 have all previously been shown to be constitutively present in the nucleus (Ragimbeau et al., 2001; Zouein et al., 2011; Nilsson et al., 2006). Activated JAK2 was shown to be present in growth hormone treated CHO cells that had been transfected with growth hormone receptor (Lobie et al., 1996). These observations may not have received much attention as they were not obviously explainable in the context of the classical model of JAK/STAT signaling.

We have previously shown that IFNγ and one of its receptor subunits, IFNGR1, are translocated to the nucleus, together with activated STAT1α as one macromolecular complex via the classical importin-dependent pathway (Ahmed and Johnson, 2006). We have further shown that IFNγ and IFNGR1 are recruited to the IFNγ-activated genes (Noon-Song et al., 2011; Ahmed and Johnson, 2006). The direct association of IFNGR1 with the promoter region of IFNγ-activated genes suggested a transcriptional/cotranscriptional role for IFNGR1 as well as its possible role in determining the specificity of gene activation by IFNγ.

The role of activated JAKs in specific gene activation of IFNγ was addressed in the context of the above macromolecular complex. ChIP followed by PCR in IFNγ treated WISH cells showed association of activated JAK1 (pJAK1) and JAK2 (pJAK2) with the IFNγ/IFNGR1/pSTAT1α complex on the same DNA sequence of the 1RF-I gene promoter (Noon-Song et al., 2011). The β-actin gene, which is not activated by IFNγ, did not show this association. Activated JAKs in the nucleus were associated with phosphorylation of H3Y41 in the GAS region of the IRF-1 promoter (Noon-Song et al., 2011). Unphosphorylated JAK2 was constitutively present in the nucleus and was capable of undergoing activation in IFNγ treated cells, most likely via nuclear IFNGR1. The IFNγ studies of activated JAK2 in the nucleus suggest that it functions in the context of the IFNγ/IFNGR1/pSTAT1α complex. This in turn provides a mechanism for controlling or identifying specific chromatin regions for pJAK2 activated epigenetic effects.

Our results here provide insight into type I IFN signaling in terms of IFN/receptor/STAT/TYK2 nuclear complexes. We showed that nonphosphorylated TYK2, like JAK2, is constitutively present in the nucleus. TYK2 is activated (pTYK2) in the nucleus only after interaction of type I IFN with the receptor complex, and, like pJAK2, phosphorylated H3Y41 at a gene (OASI) that is activated by type I IFNs, while absent from an unrelated gene (β-actin). Thus, the epigenetic event of H3Y41 phosphorylation is not unique to any particular JAK, but probably involves the JAKs that are associated with the stimulating cytokine.

Both IFNAR1 and IFNAR2 underwent nuclear translocation in type I IFN treated cells. This is in contrast to IFNγ where IFNGR2 remained associated with the cell membrane while IFNGR1 underwent nuclear translocation as part of a complex as indicated above (Ahmed and Johnson, 2006; Ahmed et al., 2003). We showed that IFNGR2 provided JAK2 to IFNGR1 via IFNγ induced increased binding affinity for IFNGR1 (Szente et al., 1995). For type I IFNs, TYK2 is associated with IFNAR1 while JAK1 is associated with IFNAR2 (Stark et al., 1998). After type I IFN treatment, pTYK2 and probably pJAK1 undergo nuclear translocation as a part of macromolecular complex that contains IFNAR1 and IFNAR2. Similar to IFNγ, we also observed nuclear translocation of type I IFN, IFNτ, by confocal microscopic analysis. Nuclear translocation of type I IFN has been known for some time (Kushnaryov et al., 1986). This observation again cannot be explained by the classical model of JAK/STAT signaling.

Since pTYK2 involvement in phosphorylation of H3Y41 was specific for a gene that is induced by type I IFNs, the question arises as to whether histone associated demethylation and acetylation show similar specificity. Focusing on trimethylated histone H3 lysine 9 (H3K9me3), we observed that in type I IFN treated cells H3K9me3 underwent demethylation in association with acetylation (H3K9ac) at the region of the OAS1 promoter. These changes in H3K9 are associated with gene activation (Berger, 2007; Mehta et al., 2011). The association of IFN receptors with pSTAT1α, pTYK2, and probably other factors in the region of genes activated by IFN provides insight into the mechanism of specific gene activation, including associated phosphorylations, methylations, demethylations, and acetylations.

In a search for precedent, it seems that our study of both type I and type II IFN signaling shares similarities to that of steroid receptor (SR) signaling. SRs are a major subset of nuclear receptors (Stanisic et al., 2010). Basically, synthesis of steroid hormones (SHs) occurs in the adrenal cortex and in gonads (Stanisic et al., 2010). Broadly, the current model of SH signaling is as follows. In the absence of hormone, cytoplasmic SR monomers are associated with heat shock proteins (HSPs) and usually possess some basal level of phosphorylation (Stanisic et al., 2010). Upon binding of hormone, SRs dissociate from HSPs, dimerize, and translocate to the nucleus where they bind to hormone receptor elements (HREs) at genes that are activated by SHs. The complex of SH/SR recruits a series of coactivators to both regulate target gene transcription as well as the associated epigenetic events that accompany gene expression. Site-specific phosphorylation of receptors occurs subsequent to hormone binding with varied kinetics, depending on the kinase and the target in the receptor complex. The kinases, while not the only components of the receptor associated co-activator complexes, are important for their action on members of the receptor complex as well as for specific epigenetic events of gene activation and thus act on histones as well as on members of the receptor complex.

Unlike SH/SR interaction, both type I and II IFN signaling initiates with ligand binding to the receptor extracellular domain. However, we have shown that IFNγ also binds to the cytoplasmic domain of receptor subunit IFNGR1 during the process of endocytosis (Szente et al., 1995; Szente et al., 1996). We showed that the N-terminus of IFNγ played the key role in recognition of IFNGR1 extracellular domain, while the C-terminus played the key role in binding to the cytoplasmic domain. This in turn led to development of IFNγ mimetics based on the C-terminus (Szente et al., 1996; Ahmed et al., 2007). We showed here that N-terminus truncations of IFNα and IFNβ resulted in loss of signaling via extracellular receptor interaction, while the same truncated IFNs with R9 attached for cell penetration possessed antiviral activity and anti-autoimmune function in EAE. These results would suggest that type I IFNs also interact with receptor cytoplasmic domain. Type I IFN cytoplasmic receptor interaction is probably more complex than that of IFNγ where only the receptor subunit IFNGR1 undergoes endocytosis, while both IFNAR1 and IFNAR2 undergo endocytosis in type I IFN signaling. The demonstration of extracellular receptor interaction for IFNs is essentially the extra step in signaling compared to SHs, which interact directly with the cytoplasmic SR. In both systems we have ligand/receptor/coactivator complexes that undergo nuclear translocation. The receptor complexes bind to promoter regions of genes that they specifically activate. Thus, the results of this and previous studies with IFNγ suggest that signaling by cytokines such as the IFNs is but a variation of steroid/steroid receptor signaling.

Materials and Methods for Examples 7 and 8

Figure 7:
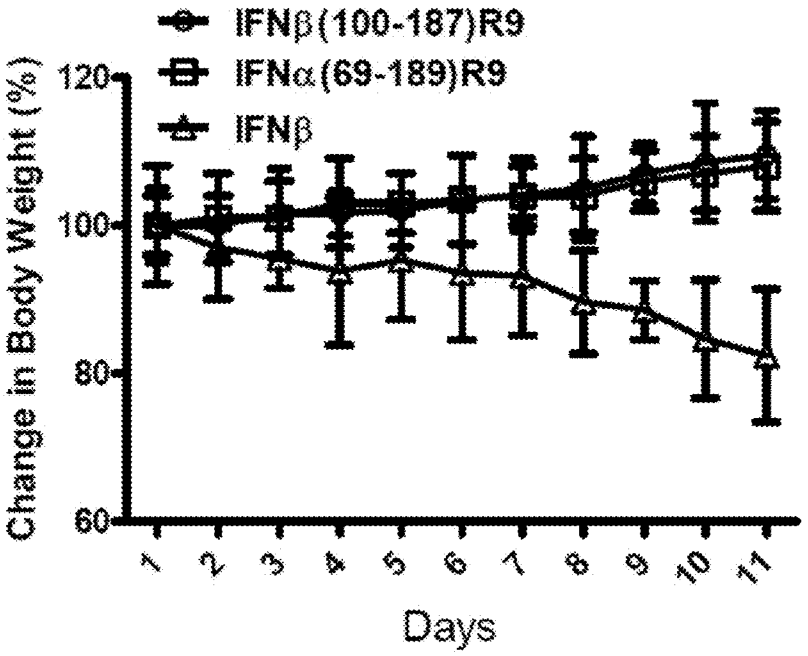
FIG. 7. Weight loss comparison. Mice (C57BL/6, n=3) were injected i.p. with IFNβ (Δ, $10^3$ U/mouse), IFNβ(100-179)R9(○), $2\times10^3$ U (200 μg), or $2\times10^3$ U (200 μg) of IFNα(69-189)R9 (□), i.p. on alternate days. Activity refers to the antiviral activity assessed by cytopathic effect of EMCV on L cells. Body weight was measured daily. The average body weight is presented as a percentage of initial weight, and the standard deviation is shown. The weight loss seen in IFNβ treated mice is not seen with IFNβ mimetic. On day 11, the difference between the IFNβ or IFNβ mimetic showed a n<0.05.

For FIG. 7 (Weight Loss) and Table 4 (Cell Counts):
Measurement of IFN Toxicity To measure toxicity induced by IFN treatment in vivo, mice (C57BL/6, n=3) were injected i.p. with IFNβ ($10^3$ U/mouse), IFNα(69-189)R9 ($2\times10^3$ U/mouse), IFNβ(100-187)R9 ($2\times10^3$ U/mouse), or PBS on alternate days. Mice were weighed daily until day 11 to see the effects of treatment on body weight. On day 11, blood was drawn from facial vein and white blood cell (WBC) counts were enumerated using a hemacytometer. Differential WBC counts were performed on Wright-Giemsa-stained blood smears.

Figure 8:
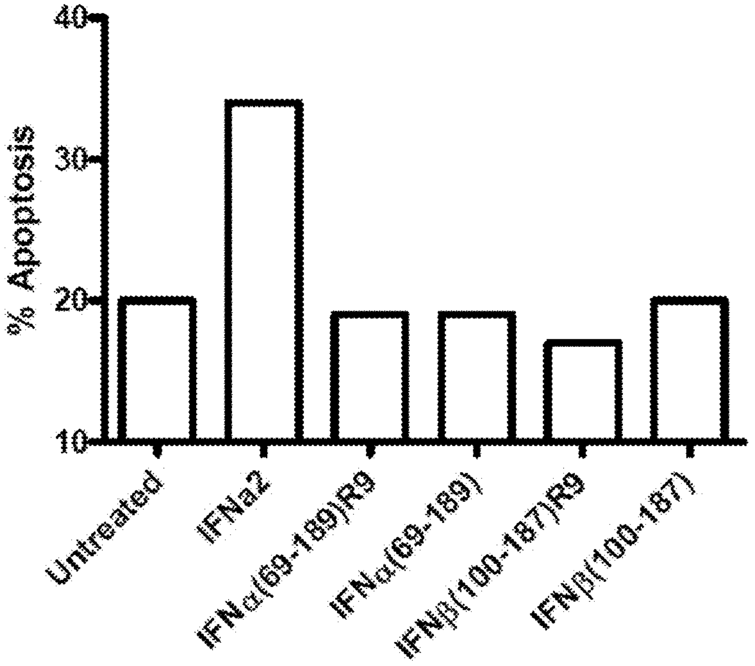
FIG. 8. Lack of apoptosis in type I IFN mimetics in comparison with intact IFNα2. WISH cells (150,000) were seeded in a 6 well plate and grown overnight. They were treated with type I IFN mimetics (100 U/ml), or IFNα2 (100 U/ml) for 4 days. Cells were doubly stained with Annexin V and propidium iodide (PI) and analyzed by flow cytometry to measure the extent of apoptosis. The data shown indicate the percentage of apoptosis based on cells staining for both Annexin V and PI from the analysis of 10,000 cells.

For FIG. 8 (Apoptosis):
Apoptosis Assay

Apoptosis on IFN and IFN mimetic treated cells was performed as previously described (Subramaniam et al., 1995). Briefly, WISH cells (150,000) were seeded in a 6 well plate and grown overnight. They were then treated with type I IFN mimetics (100 U/ml), or parent IFNs (100 U/ml) for 4 days. Cells were doubly stained with Annexin V and propidium iodide (PI), using the reagents from Invitrogen, and analyzed by flow cytometry to measure the extent of apoptosis. The data shown indicate the percentage of apoptosis based on cells staining for both Annexin V and PI from the analysis of 10,000 cells.

Figure 9:
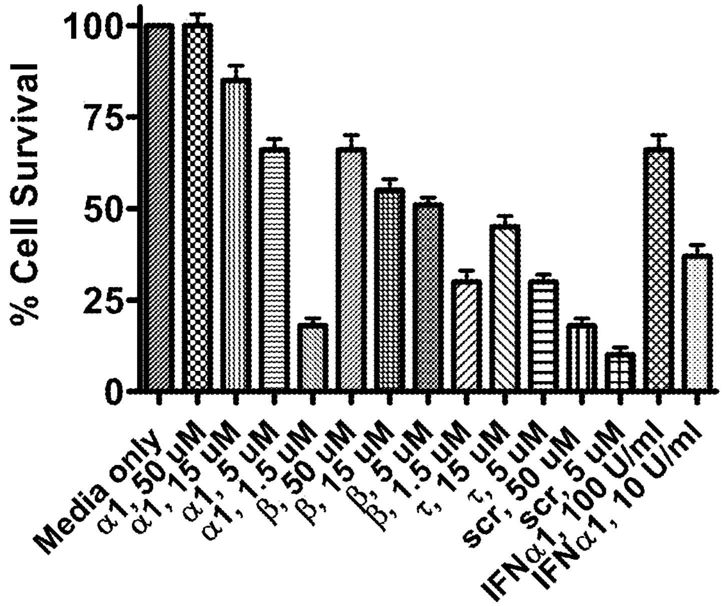
FIG. 9. Type I IFN mimetics protect cells from VSV infection. Murine L929 cells were seeded in a microtiter plate and incubated with lipo-IFNα1(152-189), lipo-IFNβ(150-187), lipo-IFNτ(151-195), scrambled peptide, or IFNα1 at the concentrations indicated for 2 hr. Cells were then infected with 0.1 m.o.i. of VSV for 24 hr, stained with crystal violet and the absorbance read.

For FIG. 9 (Antiviral Assay):
Antiviral Assay

Antiviral assays were performed by using a cytopathic effect (CPE) reduction assay using vesicular stomatitis virus (VSV). L929 cells (40,000 per well in a microtiter dish) were grown overnight. Lipo-IFNα1(152-189), lipo-IFNβ (150-187), or lipo-IFNτ(156-195) were added to cells at the concentrations indicated for 4 hr, followed by infection with VSV (moi=0.1). Virus was washed after one hr and cells were grown overnight. Cells were stained with crystal violet and read in a microtiter plate at 550 nm. Parent IFNα1 was used at the concentration indicated. "Scr" refers to a scrambled peptide corresponding to IFNτ(156-195).

Figure 10:
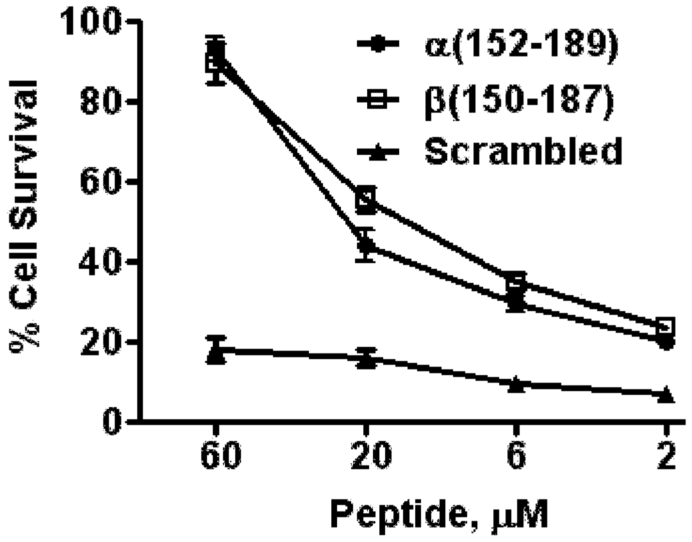
FIG. 10. Type I IFN mimetics protect against EMC virus infection. Human WISH cells (40,000 per well) were seeded in a microtiter plate and grown overnight. Treatment with IFNα and IFNβ mimetic peptides, or a control scrambled peptide was for 4 hr. Cells were infected with EMC virus (0.01 moi) for 24 hr, followed by staining with crystal violet.

For FIG. 10 (Antiviral Assay):

Antiviral assay was carried out using encephalomyocarditis (EMC) virus growing on WISH cells. Antiviral assays were performed by using a cytopathic effect (CPE) reduction assay using encephalomyocarditis (EMC) virus growing on WISH cells. WISH cells (40,000 per well in a microtiter dish) were grown overnight. Lipo-IFNα1 (152-189), lipo-IFNβ(150-187), or lipo-IFNτ(156-195) were added to cells at the concentrations indicated for 4 hr, followed by infection with EMC (moi=0.1). Virus was washed after one hr and cells were grown overnight. Cells were stained with crystal violet and read in a microtiter plate at 550 nm. Parent IFNα1 was used at the concentration indicated. "Scr" refers to a scrambled peptide corresponding to IFNτ(156-195).

Figure 11:
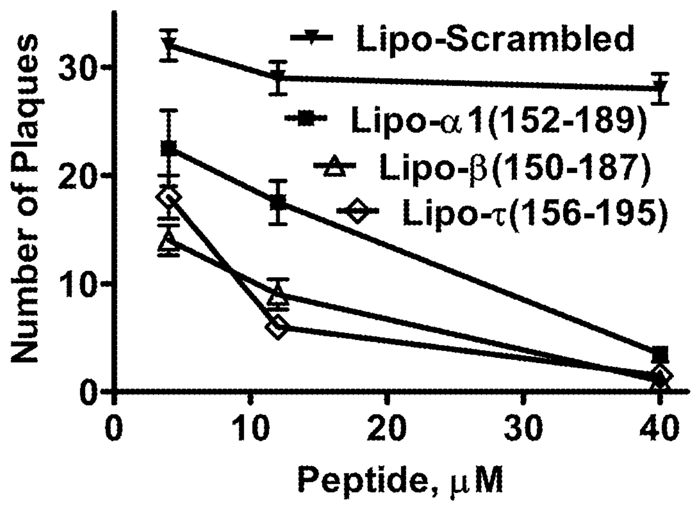
FIG. 11. Inhibition of vaccinia virus replication by type I IFN mimetics. BSC40 cells were grown to confluence and treated with the C-terminal peptides of IFNs α, β, and τ for 2 hr. Lipo—refers to the conjugated palmitic acid added for allowing these peptides to gain entry across plasma membrane. Cells were then infected with 0.01 m.o.i. of vaccinia virus for 1 hr, followed by washing and addition of fresh medium. Forty eight hours later, cells were stained with crystal violet and plaques counted. A scrambled peptide is used as a negative control. Intact IFNα1 added at 2000 U/ml did not protect against VV infection.

For FIG. 11 (Antiviral Assay):

Antiviral assay was carried out using vaccinia virus growing on BSC-40 cells. After 48 hrs of infection, cells were stained with crystal violet and plaques were counted. Antiviral assays were performed by using a cytopathic effect (CPE) reduction assay using vaccinia virus growing on BSC-40 cells. BSC-40 cells (40,000 per well in a microtiter dish) were grown overnight. Lipo-IFNα1(152-189), lipo-IFNβ(150-187), or lipo-IFNτ(156-195) were added to cells at the concentrations indicated for 4 hr, followed by infection with BSC-40 (moi=0.1). Virus was washed after one hr. After 48 hrs of infection, cells were stained with crystal violet and plaques were counted. Parent IFNα1 was used at the concentration indicated. "Scr" refers to a scrambled peptide corresponding to IFNτ(156-195).

Figure 12:
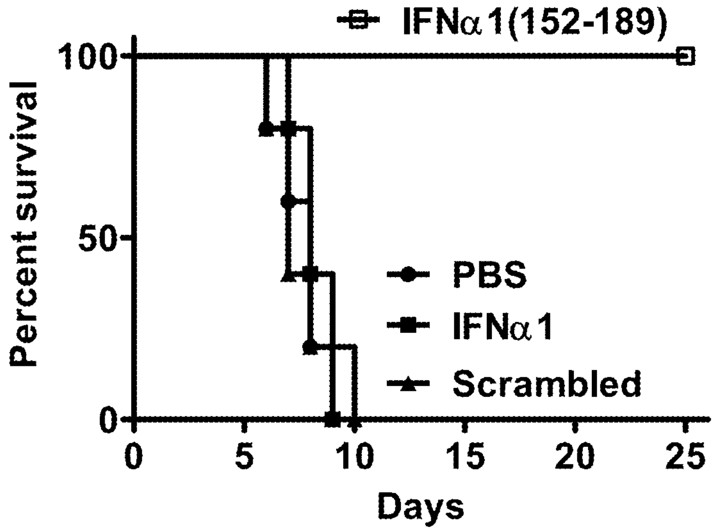
FIG. 12. Lipo-IFNα1(152-189) protects mice against vaccinia virus, while intact IFN does not. Mice (C57BL/6, n=5) were infected i.n. with $2\times10^6$ pfu of vaccinia virus. Starting on day 0, PBS, lipo-IFNα1(152-189) (200 μg), scrambled peptide (200 μg), or murine IFNα1 (2,000 U) were administered i.p. in a volume of 100 μl for six consecutive days. Survival of mice was followed.

For FIG. 12 Showing the Protection in Mice:

Female C57BL/6 mice (6-8 weeks old) were purchased from Jackson Laboratories (Bar Harbor, Me.). For intranasal administration, vaccinia virus ($10^6$ pfu) was taken in a volume of 10 μl, and 5 μl was delivered in each of the nostrils of a lightly anesthetized mouse. Following infection, mice were observed daily for signs of disease, such as lethargy, ruffled hair, weight loss, and eye secretions. Moribund mice were euthanized and counted as dead.

Figure 13:
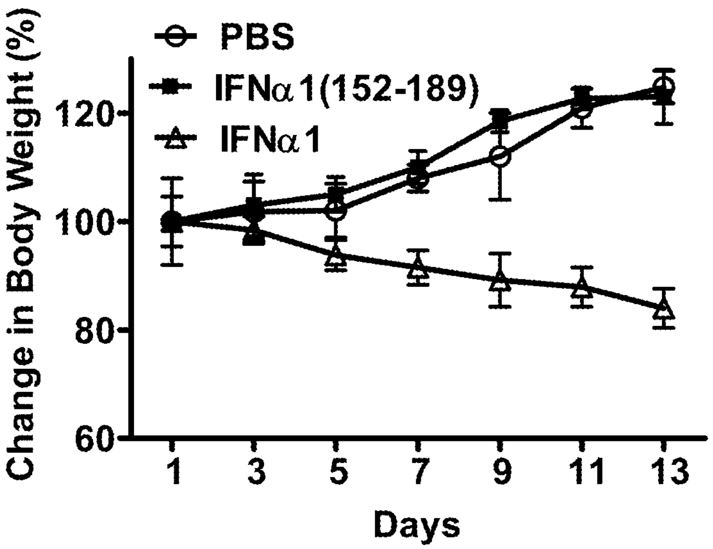
FIG. 13. Type I IFN mimetic do not show weight loss in comparison to intact IFN. Mice (C57BL/6, n=3) were injected i.p. with murine IFNα1 (Δ, $5\times10^3$ U/mouse), Lipo-IFNα(152-189), $5\times10^3$ U (100 μg, ■), or PBS (○), i.p. on alternate days. Activity refers to the antiviral activity assessed by cytopathic effect of EMCV on L cells. Body weight was measured daily. The average body weight is presented as a percentage of initial weight, and the standard deviation is shown. The weight loss seen in IFNα treated mice is not seen with IFNα mimetic. On day 11, the difference between the IFNα and IFNα mimetic showed a $p<0.05$.

For FIG. 13 (Weight Loss):

Mice (C57BL/6, n=3) were injected i.p. with murine IFNα1 ($5\times10^3$ U/mouse), Lipo-IFNα(152-189), $5\times10^3$ U (100 μg), or PBS, i.p. on alternate days. Activity refers to the antiviral activity assessed by cytopathic effect of EMCV on L cells. Body weight was measured on alternate days. The average body weight is presented as a percentage of initial weight, and the standard deviation is shown.

Following are examples that illustrate procedures for practicing the invention. These examples should not be construed as limiting. All percentages are by weight and all solvent mixture proportions are by volume unless otherwise noted.

Example 7—Type I IFN Mimetics Lack Toxicity Under Conditions where Intact IFNs are Toxic We compared mouse IFNβ with human IFNβ(100-187) R9 and IFNα1(69-189)R9 mimetics for relative toxic effects against C57BL/6 mice as reflected by weight loss (FIG. 7). Injection of mice I.P. on alternate days with 1,000 U per mouse of IFNβ resulted in approximately 15% weight loss by day 10, while mice injected with 2,000 U per mouse of IFN mimetic gained weight as would be expected under normal growth conditions (see FIG. 7). Lymphocyte counts showed a similar pattern of toxicity with 24% reduction in IFNβ injected mice and 4-9% loss in IFN mimetic treated mice (Table 4). A comparison of human IFNα2 with the mimetics on toxicity/apoptosis in WISH cells showed that IFNα2 had toxicity of approximately 14% above controls, while the mimetics showed toxicity at the level of untreated cells (FIG. 8). Thus, the IFN mimetics lacked toxicity of weight loss, lymphopenia, and cellular toxicity under conditions where the intact type I IFNs were toxic.

TABLE 4

Lymphocyte suppression seen with IFN is not observed with IFN mimetics. Lymphocyte count in mice under different treatments.

| Treatment | Lymphocytes (%) | % Reduction | Significance |
|---|---|---|---|
| PBS | 78 ± 4 | | |
| IFNα(69-189)R9 | 75 ± 3 | 4 | NS |
| IFNβ(100-187)R9 | 72 ± 5 | 9 | NS |
| IFNβ | 59 ± 6 | 24 | <0.01 |

Mice (C57BL/6, n = 3) were injected i.p. with PBS, IFN mimetics ($2\times10^3$ U in 200 μg per mouse), or IFNβ ($10^3$ U/mouse) on alternate days for ten days. On day 11, mice were bled. Blood smears were stained and lymphocytes were counted.

Example 8

We have synthesized three short type I IFN peptides based on our non-canonical model of IFN signaling. If short IFNα, IFNβ, and IFNτ C-terminal peptides of similar length to that of IFNγ(95-132) are synthesized with a palmitate (lipo-) attached for cell penetration, we predicted that they would exhibit IFN activity. We thus synthesized human lipo-IFNα1 (152-189) (SEQ ID NO:38), human β(150-187) (SEQ ID NO:39), ovine lipo-IFNτ(156-195) (SEQ ID NO:40), and lipo-IFNτ(156-195) scrambled (SEQ ID NO:41) as negative control and tested them variously for antiviral activity, the signature property of an IFN. FIG. 9 shows that all of the peptides except the scrambled IFNτ showed antiviral activity against vesicular stomatitis virus (VSV). FIG. 10 gives a dose response of lipo-IFNα1(152-189), lipo-IFNβ(150-187), and lipo-scrambled peptide against EMC virus. FIG. 11 gives a dose response of lipo-IFNα1(152-189), lipo-IFNβ(150-187), lipo-IFNτ(156-195), and lipo-scrambled peptides against vaccinia virus. Note that intact IFNs do not inhibit vaccinia virus, because of the virus induced decoy receptor that blocks binding of the IFNs to receptor extracellular domain. FIG. 12 shows that lipo-IFNα1(152-189) inhibited vaccinia virus lethal infection of mice, while the intact IFNα1 and scrambled peptide were ineffective.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 6,120,762
U.S. Pat. No. 5,770,191
U.S. Pat. No. 5,763,585
U.S. Pat. No. 5,625,136
U.S. Pat. No. 5,252,348
U.S. Pat. No. 5,106,739
U.S. Pat. No. 5,034,322
U.S. Pat. No. 4,625,014

U.S. Pat. No. 4,179,337

U.S. Published Patent Application No. 20030032594

U.S. Published Patent Application No. 20020120100

U.S. Published Patent Application No. 20020035243

Ahmed, C. M. I., K. N. Wills, B. J. Sugarman, D. Johnson, M. Ramachandra, T. L. Nagabhushan, and J. A. Howe. 2001. Selective expression of nonsecreted interferons by an adenoviral vector confers antiproliferative and antiviral properties and causes inhibition of tumor growth in nude mice. *J. Interferon and Cytokine Research.* 21: 399-408.

Ahmed, C. M., and H. M. Johnson. 2006. IFN and its receptor subunit IFNGR1 are recruited to the IFN-activated sequence element at the promoter site of IFN-activated genes: Evidence of transactivational activity in IFNGR1. *J. Immunol.* 177: 315-321.

Ahmed, C. M., M. A. Burkhart, M. G. Mujtaba, P. S. Subramaniam, H. M. and Johnson. 2003. The role of IFNgamma nuclear localization sequence in intracellular function. *J Cell Sci* 116: 3089-3098.

Ahmed, C. M., J. P. Martin, and H. M. Johnson (2007) IFN mimetic as a therapeutic for lethal vaccinia virus infection: Possible effects on innate and adaptive immune responses. *J. Immunol.* 178:4576-4583.

Ahmed, C. M., M. A. Burkhart, M. G. Mujtaba, and H. M. Johnson (2005) Peptide mimetics of interferon gamma possess antiviral properties against vaccinia and other viruses in the presence of poxvirus B8R protein. *J. Virol* 79:5632-5639.

Altschul, S. F. et al. (1990) "Basic Local Alignment Search Tool" *J. Mol. Biol.* 215:403-410.

Altschul, S. F. et al. (1997) "Gapped BLAST and PSI-BLAST: A New Generation of Protein Database Search Programs" *Nucl. Acids Res.* 25:3389-3402.

Arduino, P. G. and S. R. Porter (2008) Herpes Simplex Virus type I infection: Overview on relevant clinic-pathological features. *J. Oral Pathol. Med.* 37:107-121

Begitt, A., T. Meyer, M. van Rossum, and U. Vinkemeier. 2000. Nucleocytoplasmic translocation of STAT1 is regulated by a leucine-rich export signal in the coilded. coil domain. *Proc Natl Acad Sci USA* 97: 10418-10423. 4

Beltz, G. A., Jacobs, K. A., Eickbush, T. H., Cherbas, P. T., Kafatos, F. C. (1983) "Isolation of multigene families and determination of homologies by filter hybridization methods" *Methods of Enzymology*, R. Wu, L. Grossman and K. Moldave [eds.] Academic Press, New York 100:266-285.

Berger, S. L. 2007. The complex language of chromatin regulation during transcription. *Nature* 447: 407-412.

Burgos, J. S., E. Serrano-Saiz, I. Sastre, and F. Valdivieso (2006) ICP47 mediates viral neuroinvasiveness by induction of TAP protein following intravenous inoculation of herpes simplex virus 1 in mice. *J. Neurovirol.* 12:420-427

Chee, A. V. and B. Roizman (2004) Herpes simplex virus 1 gene products occlude the interferon signaling pathway at multiple sites. *J. Virol.* 78:4185-4196

Croker, B. A., H. Kiu, and S. E. Nicholson (2008) SOCS regulation of JAK/STAT signaling pathway. *Sem. Cell Dev. Biol.* 19:414-422

Cunningham, A. L., R. J. Diefenbach, M. Miranda-Saksena, L. Bosnjak, M. Kim, C. Jones, and M. W. Douglas (2006) The cycle of human herpes simplex virus infection: virus transport and immune control. *J. Infect. Dis.* 194:S11-S18

Dawson, M. A., A. J. Bannister, B. Gottgens, S. D. Foster, T. Bartke, A. R. Green, and T. Kouzarides. 2009. JAK2 phosphorylates histone H3Y41 and excludes HP1α from chromatin. *Nature* 461: 819-822.

de Boer, H. A., Comstock, L. J., Vasser, M. (1983) "The tac promoter: a functional hybrid derived from the trp and lac promoters" *Proc. Natl. Acad. Sci. USA* 80(1):21-25.

Decman, V., P. R. Kinchington, S. A. Harvey, and R. L. Hendricks (2005) Gamma interferon can block herpes simplex virus type 1 reactivation from latency, even in the presence of late gene expression. *J. Virol.* 79:10339-10347

Diefenbach, R. J., M. Miranda-Saksena, M. W. Douglas, and A. L. Cunningham (2008) Transport and egress of herpes simplex virus in neurons. *Rev. Med. Virol.* 18:35-51

Dorsky D. I. and C. S. Crumpacker (1987) Drugs five years later: acyclovir. *Ann. Intern. Med.* 107:859-874

Duvallet, E., L. Semerano, E. Assier, G. Falgarone, and M. C. Boissier. 2011. Interleukin-23: a key cytokine in inflammatory diseases. *Ann Med* 43: 503-511.

Edison, K. M., W. E. Hobbs, B. J. Manning, P. Carlson, N. A. and DeLuca (2002) Expression of herpes simplex virus ICP0 inhibits the induction of interferon-stimulated genes by viral infection. *J. Virol.* 76:2180-2191

Fairchild, R. L., J. W. Moorhead (1985) *J. Immunol. Meth.* 85:183-193.

Felgner, P. L., T. R. Gadek, M. Holm, R. Roman, H. W. Chan, M. Wenz, J. P. Northrop, G. M. Ringold, M. Danielsen (1987) "Lipofection: a highly efficient, lipid-mediated DNA-transfection procedure" *Proc Natl Acad Sci U.S.A.* 84(21):7413-7417.

Frey, K. G., C. M. Ahmed, R. Dabelic, E. N. Noon-Song, S. M. Haider, and H. M. Johnson (2009) HIV-1 induced SOCS-1 expression in keratinocytes: Use of a SOCS-1 antagonist to block a novel mechanism of viral immune evasion. *J. Immunol.* (in press).

Goldsmith, K., W. Chen, D. C. Johnson, R. L. and Hendricks (1998) Infected cell protein (ICP) 47 enhances herpes simplex virus neurovirulence by blocking the CD8+ T cell response. *J. Exp. Med.* 187:341-348

Gough, D. J., D. E. Levy, R. W. Johnsotone, and C. J. Clarke. 2008. IFN gamma signaling-does it mean JAK-STAT? *Cytokine Growth Factor Rev* 19: 383-394.

Halford, W. P., C. Weisend, J. Grace, M. Soboleski, D. J. Carr, J. W. Balliet, Y. Imai, T. P. Margolis, and B. M. Gebhardt (2006) ICP0 antagonizes STAT1-dependent repression of herpes simplex virus: Implications for the regulation of viral latency. *Virology J.* 3:44-49

Jager, L. D., R. Dabelic, L. W. Waiboci, L. Lau, S. M. Haider, C. M. Ahmed C M, J. Larkin, S. David, and H. M. Johnson. 2011. The kinase inhibitory region of SOCS-1 is sufficient to inhibit T-helper 17 and other immune functions in experimental allergic encephalomyelitis. *J. Neuroimmunol.* 232: 108-118.

Johnson, H. M., and C. M. Ahmed. 2006. Gamma interferon signaling: Insights to development of interferon mimetics. *Cell Mol Biol* 52: 71-76.

Johnson, H. M., E. N. Noon-Song, K. Kemppainen, and C. M. Ahmed. 2012. Steroid-like signaling by interferons: Making sense of specific gene activation by cytokines *Biochem J.* 443: In Press.

Johnson, H. M., P. S. Subramaniam, S. Olsnes, and D. A. Jans. 2004. Trafficking and signaling pathways of nuclear localizing protein ligands and, their receptors. *BioEssays* 26: 993-1004.

Jones, L. L., and D. A. Vignali. 2011. Molecular interactions within IL-6/IL-12 cytokine/receptor superfamily. *Immunol Res* 51: 5-14.

Karlin S., Altschul, S. F. (1990) "Methods for Assessing the Statistical Significance of Molecular Sequence Features by Using General Scoring Schemes" *Proc. Natl. Acad. Sci. USA* 87:2264-2268.

Karlin S., Altschul, S. F. (1993) "Applications and Statistics for Multiple High-Scoring Segments in Molecular Sequences" *Proc. Natl. Acad. Sci. USA* 90:5873-5877.

Knickelbein, J. E., K. M. Khanna, M. B. Yee, C. J. Baty, P. R. Kinchington, and R. L. Hendricks (2008) Noncytotoxic lytic granule-mediated CD8+ T cell inhibition of HSV-1 reactivation from neuronal latency. *Science* 322: 268-271

Kobayashi, T., G. Takaesu, and A. Yoshimura (2006) Malfunction of TLRs by SOCS. *Nat. Immunol.* 7:123-124.

Koelle, D. M. and L. Corey (2008) Herpes Simplex: Insights on pathogenesis and possible vaccines. *Ann. Rev. Med.* 59:381-395.

Kohler, G. and C. Milstein (1975) "Continuous cultures of fused cells secreting antibody of predefined specificity" *Nature* 256(5517):495-497.

Kushnaryov, V. M., H. S. MacDonald, J. Deburin, G. P. Lemense, J. J. Sedmark, and S. E. Grossberg. 1986. Internalization and transport of mouse beta-interferon into the cell nucleus. *J Interferon Res* 6: 241-245.

Levy, D. E., and J. E. Darnell. 2002. STATs: Transcriptional control and biological impact. *Nature Rev Mol Cell Biol.* 3: 651-662.

Lobie, P., B. Ronsin, O. Silvennoinen, L. A. Haldosen, G. Norstedt, and G. Morel. 1996. Constitutive nuclear localization of Janus kinases 1 and 2. *Endocrinology* 137: 4037-4045.

Lu, X., L. J. Huanf, and H. F. Lodish. 2008. Dimerization by a cytokine receptor is necessary for constitutive activation of JAK2V617F. *J Biol Chem* 283: 5258-5266.

Maniatis, T., Fritsch, E. F., Sambrook, J. (1982) *Molecular Cloning: A Laboratory Manual*, Cold Spring Harbor Laboratory, Cold Spring Harbor, N.Y.

Manning, M., W. H. Sawyer (1985) *Vasopressin*, pages 131-144.

Mansell, A., R. Smith, S. L. Doyle, P. Gray, J. E. Fenner, P. J. Crack et al. (2006) Suppressor of cytokine signaling 1 negatively regulates Toll-like receptor signaling by mediating Mal degradation. *Nat. Immunol.* 7:148-155

McBride, K. M., C. McDonald, and N. C. Reich. 2000. Nuclear export signal located within the DNA-binding domain of the STAT1 transcription factor. *EMBO J* 19: 6196-6206. 2

Mehta, N. T., A. D. Truax, N. H. Boyd, and S. F. Greer. Early epigenetic events regulate the adaptive immune response gene CIITA. *Epigenetics* 6: 16-25; 2011.

Melen, K., L. Kinnunen, and I. Julkunen. 2001. Arginine/lysine-rich structural element is involved in interferon-induced nuclear transport. *J. Biol. Chem.* 276: 16447-16455 3

Mikloska, Z., V. A. Danis, S. Adams, A. R. Lloyd, D. L. Adrian, and A. L. Cunningham (1998) In vivo production of cytokines and beta (C—C) chemokines in human recurrent herpes simplex lesions-do herpes simplex virus-infected keratinocytes contribute to their production? *J Infect Dis* 177:827-838

Moss, B. (2007) Poxviridae. In Fields Virology, 3rd ed. D. M. Knipe, and P. M. Howley, eds. Lippincott, Williams, and Wilkins, Philadelphia, Pa. 2905-2945.

Moss, B. and J. L. Shisler (2001) Immunology 101 at poxvirus U: immune evasion genes. *Semin. Immunol.* 13:59-66.

Mossman, K. (2005) Analysis of anti-interferon properties of the herpes simplex virus type 1 ICP0 protein. *Methods Mol Med* 116:195-205

Mujtaba, M. G., C. B. Patel, R. A. Patel, L. O. Flowers, M. A. Burkhart, L. W. Waiboci, J. Martin, M. I. Haider, C. M. Ahmed, and H. M. Johnson (2006) The gamma interferon mimetic peptide IFN-gamma (95-132) prevents encephalomyocarditis virus infection both in tissue culture and in mice. *Clin Vaccine Immunol* 13:944-952.

National Multiple Sclerosis Society Bulletin at www.nationalMSsociety.org; 2012.

Nilsson, J., G. Bjursell, and M. Kannius-Janson M. 2006. Nuclear JAK2 and transcription factor NF1-C2: a novel mechanism of prolactin signaling in mammary epithelial cells. *Mol Cell Biol* 26: 5663-5674.

Noon-Song, E. N., C. M. Ahmed, R. Dabelic, J. Canton, and H. M. Johnson. 2011. Controlling nuclear JAKs and STATs for specific gene activation by IFNγ. *Biochem Biophys Res Comm* 410: 648-653.

Palese, P. and M. L. Shaw (2007) Orthomyxoviridae: The viruses and their replication. In Fields Virology, 3rd ed. D. M. Knipe, and P. M. Howley, eds. Lippincott, Williams, and Wilkins, Philadelphia, Pa. 1647-1689.

Patel, A. R., P. Romanelli, B. Roberts, and R. S. Kirsner (2007) Treatment of herpes simplex virus infection: rationale for occlusion. *Adv. Skin Wound Care* 20:408-412

Pothlichet, J., M. Chignard, and M. Si-Tahar (2008) Cutting edge: innate immune response triggered by influenza A virus is negatively regulated by SOCS1 and SOCS3 through a RIG-1/IFNAR1-dependent pathway. *J. Immunol.* 180:2034-2038.

Racaniello, V. R. (2007) Picornaviridae: The viruses and their replication. In Fields Virology, 3rd ed. D. M. Knipe, and P. M. Howley, eds. Lippincott, Williams, and Wilkins, Philadelphia, Pa. 795-838.

Ragimbeau, J., E. Dondi, A. Vasserot, P. Romero, G. Uze, and S. Pellegrini. 2001. The receptor interaction region of TYK2 contains a motif for its nuclear localization. *J Biol Chem* 276: 30812-30818.

Roizman, B. D., Knipe, M., and Whitley, R. J. (2007) "Herpes Simplex Viruses" In *Fields Virology*, $3^{rd}$ ed. D. M. Knipe, and P. M. Howley, eds. Lippincott, Williams, and Wilkins, Philadelphia, Pa. 2501-2602

Sheridan, B. S., J. E. Knickelbein, and R. L. Hendricks (2007) CD8+ T cells and latent herpes simplex virus type 1: keeping the peace in sensory ganglia. *Expert Opin Biol Ther* 7:1323-1331

Stanisic, V., Lonard, D. M., and O'Malley, B. W. (2010) Modulation of steroid hormone receptor activity. *Prog Brain Res* 181: 153-176.

Stark, G. R., I. M. Kerr, B. R. Williams, R. H. Silverman, and R. D. Schreiber. 1998. How cells respond to interferon. *Ann Rev Biochem* 67: 227-264.

Steeg, P. S., R. N. Moore, H. M. Johnson, J. J. Oppenheim (1982) *J. Exp. Med.* 156:1780-1793.

Subramaniam, P. S., and H. M. Johnson H M. 2004. The IFNRA1 subunit of the type I IFN receptor complex contains a functional nuclear localization sequence. *FEBS Lett* 578: 207-210.

Subramaniam, P. S., and H. M. Johnson. 2002. Lipid microdomains are required sites for the selective endocytosis and nuclear translocation of IFN gamma, its receptor chain IFNGR1 and the phosphorylation and nuclear translocation of STAT1 alpha. *J Immunol* 169: 1959-1969.

Subramaniam, P. S., S. A. Khan, C. H. Pontzer, and H. M. Johnson. 1995. Differential recognition of the type I interferon receptor by interferons t and α is responsible for their disparate cytotoxicities. *Proc Natl Acad Sci USA* 92: 12270-12274.

Szente, B. E., I. J. Weiner, M. J. Jablonsky, N. R. Krishna, B. A. Tones, and J. M. Johnson. 1996. Structural requirements for agonist activity of a murine interferon-gamma as assessed by monoclonal antibodies. *J Interferon Cytokine Res* 16: 813-817.

Szente, B. E., P. S. Subramaniam, and H. M. Johnson. 1995. Identification of IFNgamma receptor binding sites for JAK2 and enhancement of binding by IFN-gamma and its C-terminal peptide IFN-gamma(95-133) *J Immunol* 155: 5617-5622.

Szente, B. E., H. M. Johnson (1994) *Biochem. Biophys. Res. Commun.* 201:215-221.

Szretter K. J., S. Gangappa, J. A. Besler, H. Zeng, H. Chen, Y. Matsuoka S. Sambhara, D. E. Swayne, T. M. Tumpey, and J. M. Katz (2009). Early control of H5N1 influenza virus replication by the type I interferon response in mice. *J. Virol.* 83: 5825-5834.

Takoka, A., Y. Mitani, H. Suemori, M. Sato, T. Yokochi, S. Noguchi, N. Tanaka, and T. Taniguchi. 2000. Cross talk between interferon gamma and alpha/beta signaling components in caveolar membrane domains. *Science* 288: 2357-2360.

Tam, J. P. (1988) "Synthetic Peptide Vaccine Design: Synthesis and Properties of a High-Density Multiple Antigenic Peptide System" *Biochemistry* 85:5409-5413.

Taniguchi, T., and A. Takaoka. 2008. Critical role for constitutive type I interferon signaling in the prevention of cellular transformation. *Cancer Sci* 7: 1-8.

Waiboci, L. W., C. M. Ahmed, M. G. Mujtaba, L. O. Flowers, J. P. Martin et al. (2007) Both the suppressor of cytokine signaling 1 (SOCS-1) kinase inhibitory region and SOCS-1 mimetic bind to JAK2 autophosphorylation site: implications for the development of a SOCS-1 antagonist. *J. Immunol.* 178:5058-5068

Wald, A. and K. Link (2002) Risk of human immunodeficiency virus infection in herpes simplex virus type 2-seropositive persons: a meta-analysis. *J. Infect. Dis.* 185: 45-52

Wei, L., G. Vahedi, H. W. Sun, W. T. Watford, H. Takatori, H. L. Ramos, H. Takahashi, J. Liang, G. Gutierrez-Cruz, C. Zang, W. Peng, J. J. O'Shea, and Y. Kanno. 2010. Discrete roles of STAT4 and STAT6 transcription factors in tuning epigenetic modifications and transcription during T helper cell differentiation. *Immunity* 32: 840-851.

Weigent, D. A., G. J. Stanton, M. P. Langford, R. E. Lloyd, S. Baron (1981) *Methods Enzymol.* 78:346-351.

Xu, D., McElroy, D., Thornburg, R. W., Wu, R. et al. (1993) "Systemic induction of a potato pin2 promoter by wounding, methyl jasmonate, and abscisic acid in transgenic rice plants" *Plant Molecular Biology* 22:573-588.

Yang, X. P., K. Ghoreschi, S. M. Steward-Tharp, J. Rodriguez-Canales, J. R. Grainger, K. Hirahara, H. W. Sun, L. Wei, G. Vahedi, Y. Kanno, J. J. O'Shea, and A. Laurence. 2011. Opposing regulation of the locus encoding IL-17 through direct, reciprocal actions of STAT3 and STAT5. *Nat Immunol* 12: 247-254.

Yasukawa, H., H. Misawa, H. Sakamoto, M. Masuhara, A. Sasaki, T. Wakioka et al. (1999) The JAK-binding protein JAB inhibits Janus tyrosine kinase activity through binding in the activation loop. *EMBO J.* 18:1309-1320

Yokota, S., N. Yokosawa, T. Okabayashi, T. Suzutani, S. Miura, K. Jimbow, and N. Fujii (2004) Induction of suppressor of cytokine signaling-3 by Herpes Simplex Virus type 1 contributes to inhibition of interferon signaling pathway. *J. Virol.* 78:6282-6286

Yoshimura, A., T. Naka, and M. Kubo (2007) SOCS proteins, cytokine signalling and immune regulation. *Nat. Rev. Immunol.* 7:454-465

Zlotnik, A., R. P. Shimonkevitz, M. L. Gefter, J. Kappler, P. Marrack (1983) *J. Immunol.* 131:2814-2820.

Zouein, F. A., R. J. Duhe, and G. W. Booz. 2011. JAKs go nuclear: Emerging role of nuclear JAK1 and JAK2 in gene expression and cell growth. *Growth Factors* 29: 245-252.

We claim:

1. An agonist peptide of a type I interferon (IFN), or a polynucleotide encoding the agonist peptide; or a polynucleotide expression construct comprising the polynucleotide encoding the agonist peptide, wherein the expression construct can express the polynucleotide encoding the peptide; or a composition comprising the agonist peptide, the polynucleotide, and/or the polynucleotide expression construct; wherein the peptide does not bind to the extracellular domain of a type I IFN receptor but does bind to the cytoplasmic domain of a type I IFN receptor, and wherein the peptide consists of the amino acid sequence of SEQ ID NO:1, SEQ ID NO:2, SEQ ID NO:3, SEQ ID NO:4, SEQ ID NO:38, SEQ ID NO:39, or SEQ ID NO:40.

2. The peptide according to claim 1, wherein the peptide comprises a protein or nucleic acid that is attached to the peptide and that targets delivery to the cell and/or that provides for translocation of the peptide across a biological membrane of the cell.

3. The peptide according to claim 1, wherein a lipophilic group is attached to the peptide.

4. The peptide according to claim 3, wherein the lipophilic group is a palmitoyl-lysine group.

5. The peptide according to claim 3, wherein the peptide comprises one or more arginine amino acids at the N-terminus of the peptide, or at the C-terminus of the peptide, or both termini of the peptide.

6. The peptide according to claim 1, wherein the peptide comprises a nuclear localization sequence (NLS) attached to the peptide.

7. The composition according to claim 1, wherein the composition comprises a suitable carrier, diluent, or buffer.

8. The composition according to claim 1, wherein the peptide or polynucleotide is encapsulated in a liposome.

9. The polynucleotide expression construct according to claim 1, wherein said expression construct comprises one or more regulatory elements.

10. The peptide according to claim 1, wherein the peptide comprises a cell-penetrating peptide (CPP) attached to the peptide.

11. The peptide according to claim 10, wherein the CPP comprises the amino acid sequence of SEQ ID NO:43.

12. The peptide according to claim 10, wherein the CPP comprises only arginine (R) or only lysine (K) amino acids.

13. The peptide according to claim 1, wherein the peptide has the same or similar biological activity as that associated with a full-length type I IFN protein.

14. The peptide according to claim 1, wherein the peptide consists of the amino acid sequence of SEQ ID NO: 1.

15. The peptide according to claim 1, wherein the peptide consists of the amino acid sequence of SEQ ID NO:2.

16. The peptide according to claim 1, wherein the peptide consists of the amino acid sequence of SEQ ID NO:3.

17. The peptide according to claim 1, wherein the peptide consists of the amino acid sequence of SEQ ID NO:4.

18. The peptide according to claim 1, wherein the peptide consists of the amino acid sequence of SEQ ID NO:38.

19. The peptide according to claim 1, wherein the peptide consists of the amino acid sequence of SEQ ID NO:39.

20. The peptide according to claim 1, wherein the peptide consists of the amino acid sequence of SEQ ID NO:40.

* * * * *

UNITED STATES PATENT AND TRADEMARK OFFICE

CERTIFICATE OF CORRECTION

PATENT NO. : 9,951,111 B2
APPLICATION NO. : 14/103564
DATED : April 24, 2018
INVENTOR(S) : Howard M. Johnson and Chulbul M. Ahmed It is certified that error appears in the above-identified patent and that said Letters Patent is hereby corrected as shown below:

In the Specification

Column 12,
Line 64, "(TAMIELU)" should read --(TAMIFLU)--.

Column 28,
Line 63, "Immunoprecipitation Cells were" should read --*immunoprecipitation* Cells were--.

Column 30,
Line 45, ""STAT1β and" should read --STAT1α and--.

Signed and Sealed this
Fourth Day of September, 2018

Andrei Iancu
*Director of the United States Patent and Trademark Office*

SEQUENCE LISTING

```
<160> NUMBER OF SEQ ID NOS: 43

<210> SEQ ID NO 1
<211> LENGTH: 121
<212> TYPE: PRT
<213> ORGANISM: Homo sapiens

<400> SEQUENCE: 1

Asn Gln Phe Gln Lys Ala Pro Ala Ile Ser Val Leu His Glu Leu Ile
1               5                   10                  15

Gln Gln Ile Phe Asn Leu Phe Thr Thr Lys Asp Ser Ser Ala Ala Trp
            20                  25                  30

Asp Glu Asp Leu Leu Asp Lys Phe Cys Thr Glu Leu Tyr Gln Gln Leu
        35                  40                  45

Asn Asp Leu Glu Ala Cys Val Met Gln Glu Glu Arg Val Gly Glu Thr
    50                  55                  60

Pro Leu Met Asn Ala Asp Ser Ile Leu Ala Val Lys Lys Tyr Phe Arg
65                  70                  75                  80

Arg Ile Thr Leu Tyr Leu Thr Glu Lys Lys Tyr Ser Pro Cys Ala Trp
                85                  90                  95

Glu Val Val Arg Ala Glu Ile Met Arg Ser Leu Ser Leu Ser Thr Asn
            100                 105                 110
```

-continued

```
Leu Gln Glu Arg Leu Arg Arg Lys Glu
        115                 120


<210> SEQ ID NO 2
<211> LENGTH: 88
<212> TYPE: PRT
<213> ORGANISM: Homo sapiens

<400> SEQUENCE: 2

Trp Asn Glu Thr Ile Val Glu Asn Leu Leu Ala Asn Val Tyr His Gln
1               5                   10                  15

Ile Asn His Leu Lys Thr Val Leu Glu Glu Lys Leu Glu Lys Glu Asp
            20                  25                  30

Phe Thr Arg Gly Lys Leu Met Ser Ser Leu His Leu Lys Arg Tyr Tyr
        35                  40                  45

Gly Arg Ile Leu His Tyr Leu Lys Ala Lys Glu Tyr Ser His Cys Ala
    50                  55                  60

Trp Thr Ile Val Arg Val Glu Ile Leu Arg Asn Phe Tyr Phe Ile Asn
65                  70                  75                  80

Arg Leu Thr Gly Tyr Leu Arg Asn
                85


<210> SEQ ID NO 3
<211> LENGTH: 130
<212> TYPE: PRT
<213> ORGANISM: Homo sapiens

<400> SEQUENCE: 3

Arg Arg Arg Arg Arg Arg Arg Arg Arg Asn Gln Phe Gln Lys Ala Pro
1               5                   10                  15

Ala Ile Ser Val Leu His Glu Leu Ile Gln Gln Ile Phe Asn Leu Phe
            20                  25                  30

Thr Thr Lys Asp Ser Ser Ala Ala Trp Asp Glu Asp Leu Leu Asp Lys
        35                  40                  45

Phe Cys Thr Glu Leu Tyr Gln Gln Leu Asn Asp Leu Glu Ala Cys Val
    50                  55                  60

Met Gln Glu Glu Arg Val Gly Glu Thr Pro Leu Met Asn Ala Asp Ser
65                  70                  75                  80

Ile Leu Ala Val Lys Lys Tyr Phe Arg Arg Ile Thr Leu Tyr Leu Thr
                85                  90                  95

Glu Lys Lys Tyr Ser Pro Cys Ala Trp Glu Val Val Arg Ala Glu Ile
            100                 105                 110

Met Arg Ser Leu Ser Leu Ser Thr Asn Leu Gln Glu Arg Leu Arg Arg
        115                 120                 125

Lys Glu
    130


<210> SEQ ID NO 4
<211> LENGTH: 97
<212> TYPE: PRT
<213> ORGANISM: Homo sapiens

<400> SEQUENCE: 4

Arg Arg Arg Arg Arg Arg Arg Arg Arg Trp Asn Glu Thr Ile Val Glu
1               5                   10                  15

Asn Leu Leu Ala Asn Val Tyr His Gln Ile Asn His Leu Lys Thr Val
            20                  25                  30
```

Leu Glu Glu Lys Leu Glu Lys Glu Asp Phe Thr Arg Gly Lys Leu Met
        35                  40                  45

Ser Ser Leu His Leu Lys Arg Tyr Tyr Gly Arg Ile Leu His Tyr Leu
    50                  55                  60

Lys Ala Lys Glu Tyr Ser His Cys Ala Trp Thr Ile Val Arg Val Glu
65                  70                  75                  80

Ile Leu Arg Asn Phe Tyr Phe Ile Asn Arg Leu Thr Gly Tyr Leu Arg
                85                  90                  95

Asn

<210> SEQ ID NO 5
<211> LENGTH: 121
<212> TYPE: PRT
<213> ORGANISM: Homo sapiens

<400> SEQUENCE: 5

Asn Gln Phe Gln Lys Ala Glu Thr Ile Pro Val Leu His Glu Met Ile
1               5                   10                  15

Gln Gln Ile Phe Asn Leu Phe Ser Thr Lys Asp Ser Ser Ala Ala Trp
            20                  25                  30

Asp Glu Thr Leu Leu Asp Lys Phe Tyr Thr Glu Leu Tyr Gln Gln Leu
        35                  40                  45

Asn Asp Leu Glu Ala Cys Val Ile Gln Gly Val Gly Val Thr Glu Thr
    50                  55                  60

Pro Leu Met Lys Glu Asp Ser Ile Leu Ala Val Arg Lys Tyr Phe Gln
65                  70                  75                  80

Arg Ile Thr Leu Tyr Leu Lys Glu Lys Lys Tyr Ser Pro Cys Ala Trp
                85                  90                  95

Glu Val Val Arg Ala Glu Ile Met Arg Ser Phe Ser Leu Ser Thr Asn
            100                 105                 110

Leu Gln Glu Ser Leu Arg Ser Lys Glu
        115                 120

<210> SEQ ID NO 6
<211> LENGTH: 121
<212> TYPE: PRT
<213> ORGANISM: Homo sapiens

<400> SEQUENCE: 6

His Gln Phe Gln Lys Ala Gln Ala Ile Ser Val Leu His Glu Met Ile
1               5                   10                  15

Gln Gln Thr Phe Asn Leu Phe Ser Thr Glu Asp Ser Ser Ala Ala Trp
            20                  25                  30

Glu Gln Ser Leu Leu Glu Lys Phe Ser Thr Glu Leu Tyr Gln Gln Leu
        35                  40                  45

Asn Asp Leu Glu Ala Cys Val Ile Gln Glu Val Gly Val Glu Glu Thr
    50                  55                  60

Pro Leu Met Asn Glu Asp Ser Ile Leu Ala Val Arg Lys Tyr Phe Gln
65                  70                  75                  80

Arg Ile Thr Leu Tyr Leu Thr Glu Lys Lys Tyr Ser Pro Cys Ala Trp
                85                  90                  95

Glu Val Val Arg Ala Glu Ile Met Arg Ser Leu Ser Phe Ser Thr Asn
            100                 105                 110

Leu Gln Lys Arg Leu Arg Arg Lys Asp
        115                 120

<210> SEQ ID NO 7
<211> LENGTH: 38
<212> TYPE: PRT
<213> ORGANISM: Artificial sequence
<220> FEATURE:
<223> OTHER INFORMATION: MuIFN-gamma(95-132)

<400> SEQUENCE: 7

Ala Lys Phe Glu Val Asn Asn Pro Gln Val Gln Arg Gln Ala Phe Asn
1 5 10 15

Glu Leu Ile Arg Val Val His Gln Leu Leu Pro Glu Ser Ser Leu Arg
20 25 30

Lys Arg Lys Arg Ser Arg
35

<210> SEQ ID NO 8
<211> LENGTH: 40
<212> TYPE: PRT
<213> ORGANISM: Artificial sequence
<220> FEATURE:
<223> OTHER INFORMATION: huIFN-gamma (95-134) peptide

<400> SEQUENCE: 8

Leu Thr Asn Tyr Ser Val Thr Asp Leu Asn Val Gln Arg Lys Ala Ile
1 5 10 15

His Glu Leu Ile Gln Val Met Ala Glu Leu Ser Pro Ala Ala Lys Thr
20 25 30

Gly Lys Arg Lys Arg Ser Gln Met
35 40

<210> SEQ ID NO 9
<211> LENGTH: 12
<212> TYPE: PRT
<213> ORGANISM: Artificial sequence
<220> FEATURE:
<223> OTHER INFORMATION: Tkip peptide

<400> SEQUENCE: 9

Trp Leu Val Phe Phe Val Ile Phe Tyr Phe Phe Arg
1 5 10

<210> SEQ ID NO 10
<211> LENGTH: 16
<212> TYPE: PRT
<213> ORGANISM: Artificial sequence
<220> FEATURE:
<223> OTHER INFORMATION: SOCS1-KIR peptide

<400> SEQUENCE: 10

Asp Thr His Phe Arg Thr Phe Arg Ser His Ser Asp Tyr Arg Arg Ile
1 5 10 15

<210> SEQ ID NO 11
<211> LENGTH: 189
<212> TYPE: PRT
<213> ORGANISM: Homo sapiens

<400> SEQUENCE: 11

Met Ala Ser Pro Phe Ala Leu Leu Met Val Leu Val Val Leu Ser Cys
1 5 10 15

Lys Ser Ser Cys Ser Leu Gly Cys Asp Leu Pro Glu Thr His Ser Leu
20 25 30

Asp Asn Arg Arg Thr Leu Met Leu Leu Ala Gln Met Ser Arg Ile Ser
35 40 45

```
Pro Ser Ser Cys Leu Met Asp Arg His Asp Phe Gly Phe Pro Gln Glu
    50                  55                  60

Glu Phe Asp Gly Asn Gln Phe Gln Lys Ala Pro Ala Ile Ser Val Leu
65                  70                  75                  80

His Glu Leu Ile Gln Gln Ile Phe Asn Leu Phe Thr Thr Lys Asp Ser
                85                  90                  95

Ser Ala Ala Trp Asp Glu Asp Leu Leu Asp Lys Phe Cys Thr Glu Leu
            100                 105                 110

Tyr Gln Gln Leu Asn Asp Leu Glu Ala Cys Val Met Gln Glu Glu Arg
        115                 120                 125

Val Gly Glu Thr Pro Leu Met Asn Ala Asp Ser Ile Leu Ala Val Lys
    130                 135                 140

Lys Tyr Phe Arg Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Leu Ser Thr Asn Leu Gln Glu Arg Leu Arg Arg Lys Glu
            180                 185


<210> SEQ ID NO 12
<211> LENGTH: 187
<212> TYPE: PRT
<213> ORGANISM: Homo sapiens

<400> SEQUENCE: 12

Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
            180                 185


<210> SEQ ID NO 13
<211> LENGTH: 20
<212> TYPE: PRT
<213> ORGANISM: Artificial sequence
<220> FEATURE:
<223> OTHER INFORMATION: a histone H3 peptide
```

<220> FEATURE:
<221> NAME/KEY: MOD_RES
<222> LOCATION: (9)..(9)
<223> OTHER INFORMATION: PHOSPHORYLATION

<400> SEQUENCE: 13

Gly Gly Val Lys Lys Pro His Arg Tyr Arg Pro Gly Thr Val Ala Leu
1               5                   10                  15

Arg Glu Ile Arg
            20

<210> SEQ ID NO 14
<211> LENGTH: 20
<212> TYPE: DNA
<213> ORGANISM: Artificial sequence
<220> FEATURE:
<223> OTHER INFORMATION: a primer for amplifying human OAS1 promoter region

<400> SEQUENCE: 14
cattgacagg agagagagtg 20

<210> SEQ ID NO 15
<211> LENGTH: 20
<212> TYPE: DNA
<213> ORGANISM: Artificial sequence
<220> FEATURE:
<223> OTHER INFORMATION: a primer for amplifying human OAS1 promoter region

<400> SEQUENCE: 15
tcaggggagt gtctgatttg 20

<210> SEQ ID NO 16
<211> LENGTH: 25
<212> TYPE: DNA
<213> ORGANISM: Artificial sequence
<220> FEATURE:
<223> OTHER INFORMATION: a primer for amplifying human beta-actin promoter region

<400> SEQUENCE: 16
ctcgctctcg ctcttttttt ttttc 25

<210> SEQ ID NO 17
<211> LENGTH: 21
<212> TYPE: DNA
<213> ORGANISM: Artificial sequence
<220> FEATURE:
<223> OTHER INFORMATION: a primer for amplifying human beta-actin promoter region

<400> SEQUENCE: 17
ctcgagccat aaaaggcaac t 21

<210> SEQ ID NO 18
<211> LENGTH: 4
<212> TYPE: PRT
<213> ORGANISM: Artificial sequence
<220> FEATURE:
<223> OTHER INFORMATION: a nuclear localization sequence of IFNAR2

<400> SEQUENCE: 18

Arg Lys Lys Lys
1

-continued

<210> SEQ ID NO 19
<211> LENGTH: 15
<212> TYPE: PRT
<213> ORGANISM: Artificial sequence
<220> FEATURE:
<223> OTHER INFORMATION: cell-penetrating peptide PTD

<400> SEQUENCE: 19

```
Arg Gln Ile Lys Trp Phe Gln Asn Arg Arg Met Lys Trp Lys Lys
1               5                   10                  15
```

<210> SEQ ID NO 20
<211> LENGTH: 11
<212> TYPE: PRT
<213> ORGANISM: Artificial sequence
<220> FEATURE:
<223> OTHER INFORMATION: cell-penetrating peptide TAT

<400> SEQUENCE: 20

```
Tyr Gly Arg Lys Lys Arg Arg Gln Arg Arg Arg
1               5                   10
```

<210> SEQ ID NO 21
<211> LENGTH: 18
<212> TYPE: PRT
<213> ORGANISM: Artificial sequence
<220> FEATURE:
<223> OTHER INFORMATION: cell-penetrating peptide SynB1

<400> SEQUENCE: 21

```
Arg Gly Gly Arg Leu Ser Tyr Ser Arg Arg Arg Phe Ser Thr Ser Thr
1               5                   10                  15

Gly Arg
```

<210> SEQ ID NO 22
<211> LENGTH: 10
<212> TYPE: PRT
<213> ORGANISM: Artificial sequence
<220> FEATURE:
<223> OTHER INFORMATION: cell-penetrating peptide SynB3

<400> SEQUENCE: 22

```
Arg Arg Leu Ser Tyr Ser Arg Arg Arg Phe
1               5                   10
```

<210> SEQ ID NO 23
<211> LENGTH: 12
<212> TYPE: PRT
<213> ORGANISM: Artificial sequence
<220> FEATURE:
<223> OTHER INFORMATION: cell-penetrating peptide PTD-4

<400> SEQUENCE: 23

```
Pro Ile Arg Arg Arg Lys Lys Leu Arg Arg Leu Lys
1               5                   10
```

<210> SEQ ID NO 24
<211> LENGTH: 12
<212> TYPE: PRT
<213> ORGANISM: Artificial sequence
<220> FEATURE:
<223> OTHER INFORMATION: cell-penetrating peptide PTD-5

<400> SEQUENCE: 24

```
Arg Arg Gln Arg Arg Thr Ser Lys Leu Met Lys Arg
1               5                   10
```

<210> SEQ ID NO 25
<211> LENGTH: 15
<212> TYPE: PRT
<213> ORGANISM: Artificial sequence
<220> FEATURE:
<223> OTHER INFORMATION: cell-penetrating peptide FHV Coat-(35-49)

<400> SEQUENCE: 25

Arg Arg Arg Arg Asn Arg Thr Arg Arg Asn Arg Arg Arg Val Arg
1 5 10 15

<210> SEQ ID NO 26
<211> LENGTH: 19
<212> TYPE: PRT
<213> ORGANISM: Artificial sequence
<220> FEATURE:
<223> OTHER INFORMATION: cell-penetrating peptide BMV Gag-(7-25)

<400> SEQUENCE: 26

Lys Met Thr Arg Ala Gln Arg Arg Ala Ala Ala Arg Arg Asn Arg Trp
1 5 10 15

Thr Ala Arg

<210> SEQ ID NO 27
<211> LENGTH: 13
<212> TYPE: PRT
<213> ORGANISM: Artificial sequence
<220> FEATURE:
<223> OTHER INFORMATION: cell-penetrating peptide HTLV-II Rex-(4-16)

<400> SEQUENCE: 27

Thr Arg Arg Gln Arg Thr Arg Arg Ala Arg Arg Asn Arg
1 5 10

<210> SEQ ID NO 28
<211> LENGTH: 13
<212> TYPE: PRT
<213> ORGANISM: Artificial sequence
<220> FEATURE:
<223> OTHER INFORMATION: cell-penetrating peptide D-Tat

<400> SEQUENCE: 28

Gly Arg Lys Lys Arg Arg Gln Arg Arg Arg Pro Pro Gln
1 5 10

<210> SEQ ID NO 29
<211> LENGTH: 13
<212> TYPE: PRT
<213> ORGANISM: Artificial sequence
<220> FEATURE:
<223> OTHER INFORMATION: cell-penetrating peptide R9-Tat

<400> SEQUENCE: 29

Gly Arg Arg Arg Arg Arg Arg Arg Arg Arg Pro Pro Gln
1 5 10

<210> SEQ ID NO 30
<211> LENGTH: 27
<212> TYPE: PRT
<213> ORGANISM: Artificial sequence
<220> FEATURE:
<223> OTHER INFORMATION: cell-penetrating peptide Transportan

<400> SEQUENCE: 30

Gly Trp Thr Leu Asn Ser Ala Gly Tyr Leu Leu Gly Lys Ile Asn Leu
1 5 10 15

Lys Ala Leu Ala Ala Leu Ala Lys Lys Ile Leu
20 25

<210> SEQ ID NO 31
<211> LENGTH: 17
<212> TYPE: PRT
<213> ORGANISM: Artificial sequence
<220> FEATURE:
<223> OTHER INFORMATION: cell-penetrating peptide MAP

<400> SEQUENCE: 31

Lys Leu Ala Leu Lys Leu Ala Leu Lys Leu Ala Leu Ala Leu Lys Leu
1 5 10 15

Ala

<210> SEQ ID NO 32
<211> LENGTH: 27
<212> TYPE: PRT
<213> ORGANISM: Artificial sequence
<220> FEATURE:
<223> OTHER INFORMATION: cell-penetrating peptide SBP

<400> SEQUENCE: 32

Met Gly Leu Gly Leu His Leu Leu Val Leu Ala Ala Ala Leu Gln Gly
1 5 10 15

Ala Trp Ser Gln Pro Lys Lys Lys Arg Lys Val
20 25

<210> SEQ ID NO 33
<211> LENGTH: 27
<212> TYPE: PRT
<213> ORGANISM: Artificial sequence
<220> FEATURE:
<223> OTHER INFORMATION: cell-penetrating peptide FBP

<400> SEQUENCE: 33

Gly Ala Leu Phe Leu Gly Trp Leu Gly Ala Ala Gly Ser Thr Met Gly
1 5 10 15

Ala Trp Ser Gln Pro Lys Lys Lys Arg Lys Val
20 25

<210> SEQ ID NO 34
<211> LENGTH: 27
<212> TYPE: PRT
<213> ORGANISM: Artificial sequence
<220> FEATURE:
<223> OTHER INFORMATION: cell-penetrating peptide MPG

<400> SEQUENCE: 34

Gly Ala Leu Phe Leu Gly Phe Leu Gly Ala Ala Gly Ser Thr Met Gly
1 5 10 15

Ala Trp Ser Gln Pro Lys Lys Lys Arg Lys Val
20 25

<210> SEQ ID NO 35
<211> LENGTH: 27
<212> TYPE: PRT
<213> ORGANISM: Artificial sequence
<220> FEATURE:
<223> OTHER INFORMATION: cell-penetrating peptide MPG(delta-NLS)

<400> SEQUENCE: 35

Gly Ala Leu Phe Leu Gly Phe Leu Gly Ala Ala Gly Ser Thr Met Gly
1 5 10 15

Ala Trp Ser Gln Pro Lys Ser Lys Arg Lys Val
20 25

<210> SEQ ID NO 36
<211> LENGTH: 21
<212> TYPE: PRT
<213> ORGANISM: Artificial sequence
<220> FEATURE:
<223> OTHER INFORMATION: cell-penetrating peptide Pep-1

<400> SEQUENCE: 36

Lys Glu Thr Trp Trp Glu Thr Trp Trp Thr Glu Trp Ser Gln Pro Lys
1 5 10 15

Lys Lys Arg Lys Val
20

<210> SEQ ID NO 37
<211> LENGTH: 21
<212> TYPE: PRT
<213> ORGANISM: Artificial sequence
<220> FEATURE:
<223> OTHER INFORMATION: cell-penetrating peptide Pep-2

<400> SEQUENCE: 37

Lys Glu Thr Trp Phe Glu Thr Trp Phe Thr Glu Trp Ser Gln Pro Lys
1 5 10 15

Lys Lys Arg Lys Val
20

<210> SEQ ID NO 38
<211> LENGTH: 38
<212> TYPE: PRT
<213> ORGANISM: Homo sapiens

<400> SEQUENCE: 38

Leu Tyr Leu Thr Glu Lys Lys Tyr Ser Pro Cys Ala Trp Glu Val Val
1 5 10 15

Arg Ala Glu Ile Met Arg Ser Leu Ser Leu Ser Thr Asn Leu Gln Glu
20 25 30

Arg Leu Arg Arg Lys Glu
35

<210> SEQ ID NO 39
<211> LENGTH: 38
<212> TYPE: PRT
<213> ORGANISM: Homo sapiens

<400> SEQUENCE: 39

Ile Leu His Tyr Leu Lys Ala Lys Glu Tyr Ser His Cys Ala Trp Thr
1 5 10 15

Ile Val Arg Val Glu Ile Leu Arg Asn Phe Tyr Phe Ile Asn Arg Leu
20 25 30

Thr Gly Tyr Leu Arg Asn
35

<210> SEQ ID NO 40
<211> LENGTH: 40
<212> TYPE: PRT
<213> ORGANISM: Ovis aries

<400> SEQUENCE: 40

Glu Lys Gly Tyr Ser Asp Cys Ala Trp Glu Ile Val Arg Val Glu Met

-continued

```
1               5                   10                  15

Met Arg Ala Leu Thr Ser Ser Thr Thr Leu Gln Lys Arg Leu Thr Lys
            20                  25                  30

Thr Gly Gly Asp Leu Asn Ser Pro
        35                  40


<210> SEQ ID NO 41
<211> LENGTH: 41
<212> TYPE: PRT
<213> ORGANISM: Artificial sequence
<220> FEATURE:
<223> OTHER INFORMATION: a peptide having a scrambled sequence of the
      lipo-IFNtau peptide

<400> SEQUENCE: 41

Met Ala Val Lys Leu Gly Thr Leu Asn Gly Met Tyr Val Trp Leu Cys
1               5                   10                  15

Lys Ser Arg Ser Thr Thr Cys Gly Ser Glu Asp Ile Glu Val Lys Leu
            20                  25                  30

Glu Pro Ala Arg Gln Met Asp Thr Arg
        35                  40


<210> SEQ ID NO 42
<211> LENGTH: 195
<212> TYPE: PRT
<213> ORGANISM: Ovis aries

<400> SEQUENCE: 42

Met Ala Phe Val Leu Ser Leu Leu Met Ala Leu Val Leu Val Ser Tyr
1               5                   10                  15

Gly Pro Gly Gly Ser Leu Gly Cys Tyr Leu Ser Arg Lys Leu Met Leu
            20                  25                  30

Asp Ala Arg Glu Asn Leu Lys Leu Leu Asp Arg Met Asn Arg Leu Ser
        35                  40                  45

Pro His Ser Cys Leu Gln Asp Arg Lys Asp Phe Gly Leu Pro Gln Glu
    50                  55                  60

Met Val Glu Gly Asp Gln Leu Gln Lys Asp Gln Ala Phe Pro Val Leu
65                  70                  75                  80

Tyr Glu Met Leu Gln Gln Ser Phe Asn Leu Phe Tyr Thr Glu His Ser
                85                  90                  95

Ser Ala Ala Trp Asp Thr Thr Leu Leu Glu Gln Leu Cys Thr Gly Leu
            100                 105                 110

Gln Gln Gln Leu Asp His Leu Asp Thr Cys Arg Gly Gln Val Met Gly
        115                 120                 125

Glu Glu Asp Ser Glu Leu Gly Asn Met Asp Pro Ile Val Thr Val Lys
    130                 135                 140

Lys Tyr Phe Gln Gly Ile Tyr Asp Tyr Leu Gln Glu Lys Gly Tyr Ser
145                 150                 155                 160

Asp Cys Ala Trp Glu Ile Val Arg Val Glu Met Met Arg Ala Leu Thr
                165                 170                 175

Val Ser Thr Thr Leu Gln Lys Arg Leu Thr Lys Met Gly Gly Asp Leu
            180                 185                 190

Asn Ser Pro
        195


<210> SEQ ID NO 43
<211> LENGTH: 9
<212> TYPE: PRT
```

-continued

```
<213> ORGANISM: Artificial sequence
<220> FEATURE:
<223> OTHER INFORMATION: cell-penetrating peptide (R)9

<400> SEQUENCE: 43

Arg Arg Arg Arg Arg Arg Arg Arg Arg
1               5
```